(12) United States Patent
Ben et al.

(10) Patent No.: US 12,357,656 B2
(45) Date of Patent: Jul. 15, 2025

(54) AMORPHOUS CALCIUM CARBONATE FOR IMPROVING ATHLETIC PERFORMANCE

(71) Applicant: AMORPHICAL LTD, Ness Ziona (IL)

(72) Inventors: Yossi Ben, Moshav Zofer (IL); Yigal Dov Blum, San Jose, CA (US)

(73) Assignee: AMORPHICAL LTD, Ness Ziiona (IL)

( * ) Notice: Subject to any disclaimer, the term of this patent is extended or adjusted under 35 U.S.C. 154(b) by 721 days.

(21) Appl. No.: 17/624,612

(22) PCT Filed: Jul. 23, 2020

(86) PCT No.: PCT/IL2020/050818
§ 371 (c)(1),
(2) Date: Jan. 4, 2022

(87) PCT Pub. No.: WO2021/014448
PCT Pub. Date: Jan. 28, 2021

(65) Prior Publication Data
US 2022/0313729 A1    Oct. 6, 2022

Related U.S. Application Data

(60) Provisional application No. 62/877,316, filed on Jul. 23, 2019.

(51) Int. Cl.
| A61K 33/10 | (2006.01) |
| A23L 33/00 | (2016.01) |
| A23L 33/16 | (2016.01) |
| A61K 9/00 | (2006.01) |
| A61P 43/00 | (2006.01) |

(52) U.S. Cl.
CPC .............. *A61K 33/10* (2013.01); *A23L 33/16* (2016.08); *A23L 33/30* (2016.08); *A61K 9/006* (2013.01); *A61P 43/00* (2018.01)

(58) Field of Classification Search
None
See application file for complete search history.

(56) References Cited

U.S. PATENT DOCUMENTS

| 4,199,496 | A | 4/1980 | Johnson |
| 4,237,147 | A | 12/1980 | Merten |
| 4,757,017 | A | 7/1988 | Cheung |
| 4,964,894 | A | 10/1990 | Freepons |
| 5,437,857 | A | 8/1995 | Tung |
| 5,460,803 | A | 10/1995 | Ung |
| 5,562,895 | A | 10/1996 | Tung |
| 5,886,012 | A | 3/1999 | Pang |
| 6,265,200 | B1 | 7/2001 | De Leys |
| 6,348,571 | B1 | 2/2002 | Redei |
| 6,569,472 | B1 | 5/2003 | Zyck |
| 7,666,673 | B2 | 2/2010 | Shinohara |
| 8,324,301 | B2 | 12/2012 | Cavalier |
| 8,603,514 | B2 | 12/2013 | Yang |
| 8,617,590 | B2 | 12/2013 | Blendermann |
| 8,728,533 | B2 | 5/2014 | Ben |
| 8,802,160 | B2 | 8/2014 | Bentov |
| 8,895,309 | B2 | 11/2014 | Kaspar |
| 8,906,996 | B2 | 12/2014 | Vucak |
| 9,149,494 | B2 | 10/2015 | Sagi |
| 9,192,601 | B2 | 11/2015 | Evans |
| 9,550,878 | B2 | 1/2017 | Meiron |
| 9,950,013 | B2 | 4/2018 | Van Norren |
| 11,052,108 | B2 | 7/2021 | Ben |
| 2003/0077604 | A1 | 4/2003 | Sun |
| 2004/0028748 | A1 | 2/2004 | Sasaya |
| 2004/0234614 | A1 | 11/2004 | Strong |
| 2006/0165784 | A1 | 7/2006 | Zhao |
| 2007/0041506 | A1 | 2/2007 | Bottino |
| 2007/0191963 | A1 | 8/2007 | Winterbottom |
| 2008/0095819 | A1 | 4/2008 | Gourdie |
| 2008/0160086 | A1 | 7/2008 | Farber |
| 2008/0226715 | A1 | 9/2008 | Cha |
| 2010/0096330 | A1 | 4/2010 | Gotch |
| 2011/0313052 | A1 | 12/2011 | Engqvist |
| 2013/0190441 | A1 | 7/2013 | Vucak |
| 2014/0161784 | A1 | 6/2014 | Westerlund |
| 2015/0056306 | A1 | 2/2015 | Sagi |
| 2015/0250784 | A1 | 9/2015 | Malik |
| 2018/0140631 | A1 | 5/2018 | Ben |
| 2019/0030068 | A1 | 1/2019 | Ben |

FOREIGN PATENT DOCUMENTS

| CA | 2806131 A1 | 2/2012 |
| CN | 1708240 A | 12/2005 |
| CN | 101314031 A | 12/2008 |
| CN | 101580260 A | 11/2009 |

(Continued)

OTHER PUBLICATIONS

Aartsma-Rus and van Putten (2014) Assessing functional performance in the mdx mouse model. J Vis Exp (85): 51303.
Ackerman et al., (1985) Toxicity testing for human in vitro fertilization programs. J In Vitro Fert Embryo Transf 2(3): 132-137.
Addadi et al., (2003) Taking Advantage of Disorder: Amorphous Calcium Carbonate and its Roles in Biomineralization. Advanced Materials 15(12): 959-970.
Agarwal and Sekhon (2010) The role of antioxidant therapy in the treatment of male infertility. Hum Fertil (Camb) 13(4):217-225.
Akamatsu, "Oriental Drugs, New Revision", 1st Ed. Ishiyaku Shuppan K. K., 1970, p. 911.

(Continued)

*Primary Examiner* — Robert A Wax
*Assistant Examiner* — Quanglong N Truong
(74) *Attorney, Agent, or Firm* — Dorsey & Whitney LLP

(57) ABSTRACT

The present invention provides methods for enhancing and improving athletic performances of both professional and non-professional athletes by administering compositions comprising stabilized amorphous calcium carbonate. The enhanced athletic performances result among others from enhanced muscle performances, enhanced recovery and endurance.

19 Claims, 6 Drawing Sheets

(56) References Cited

FOREIGN PATENT DOCUMENTS

| | | |
|---|---|---|
| CN | 101969962 A | 2/2011 |
| CN | 102085356 A | 6/2011 |
| CN | 102604895 A | 7/2012 |
| CN | 103663532 B | 10/2015 |
| EP | 0052677 A1 | 6/1982 |
| EP | 0628017 A1 | 12/1994 |
| EP | 1666046 A1 | 6/2006 |
| EP | 2739166 B1 | 2/2020 |
| EP | 3349596 B1 | 4/2020 |
| GB | 2217988 A | 11/1989 |
| JP | H01156985 A | 6/1989 |
| JP | H09009871 A | 1/1997 |
| JP | H10236957 A | 9/1998 |
| JP | 2002504140 A | 2/2002 |
| JP | 2003292453 A | 10/2003 |
| JP | 2004081739 A | 3/2004 |
| JP | 2008500332 A | 1/2008 |
| JP | 2008545845 A | 12/2008 |
| JP | 2011501676 A | 1/2011 |
| KR | 1020020082813 A | 10/2002 |
| KR | 1020050110119 A | 11/2005 |
| KZ | 26035 A4 | 9/2012 |
| RU | 94022264 A | 5/1996 |
| RU | 2550865 C1 | 5/2015 |
| WO | 9404460 A1 | 3/1994 |
| WO | 9724069 A1 | 7/1997 |
| WO | 9857656 A1 | 12/1998 |
| WO | 2005025581 A1 | 3/2005 |
| WO | 2005041921 A2 | 5/2005 |
| WO | 2005115414 A2 | 12/2005 |
| WO | 2006043966 A2 | 4/2006 |
| WO | 2006131497 A1 | 12/2006 |
| WO | 2007048811 A1 | 5/2007 |
| WO | 2008041236 A2 | 4/2008 |
| WO | 2009053967 A1 | 4/2009 |
| WO | 2009087553 A1 | 7/2009 |
| WO | 2010093285 A1 | 8/2010 |
| WO | 2012030664 A1 | 3/2012 |
| WO | 2012149173 A2 | 11/2012 |
| WO | 2013088440 A1 | 6/2013 |
| WO | 2014024191 A1 | 2/2014 |
| WO | 2014122658 A1 | 8/2014 |
| WO | 2016016893 A1 | 2/2016 |
| WO | 2016016895 A1 | 2/2016 |
| WO | 2016193982 A1 | 12/2016 |
| WO | 2016193983 A1 | 12/2016 |
| WO | 2017125917 A1 | 7/2017 |
| WO | 2017125918 A1 | 7/2017 |

OTHER PUBLICATIONS

Akiva-Tal et al., (2011) In situ molecular NMR picture of bioavailable calcium stabilized as amorphous CaCO3 biomineral in crayfish gastroliths. Proc Natl Acad Sci U S A 108(36): 14763-14768.

Amjad and Hooley (1994) Effect of antiscalants on the precipitation of calcium carbonate in aqueous solutions. Tenside, Surfactants, Detergents, 31(1): 12-17.

Amann and Waberski (2014) Computer-assisted sperm analysis (CASA): capabilities and potential developments. Theriogenology 81(1): 5-17.

Bajpai et al., (2004) Pseudohypoparathyroidism Presenting with Bony Deformities Resembling Rickets. Indian Journal of Pediatrics 71(4):345-347.

Ben-Aharon et al., (2013) Bisphosphonates in the adjuvant setting of breast cancer therapy-effect on survival: a systematic review and meta-analysis. PloS One 8(8): e70044.

Bentov et al., (2010) Stabilization of amorphous calcium carbonate by phosphate rich organic matrix proteins and by single phosphoamino acids. Journal of Structural Biology 171(2): 207-215.

Bhoumik et al., (2014) Optimum calcium concentration: a crucial factor in regulating sperm motility in vitro. Cell Biochem Biophys 70(2): 1177-1183.

Boland et al., (1996) Skeletal, cardiac, and smooth muscle failure in Duchenne muscular dystrophy. Pediatr Neurol 14 (1): 7-12, abstract.

Bonetto et al., (2015) Assessment of muscle mass and strength in mice. Bonekey Rep 4: 732.

Brusentsev et al., (2014) Traditional and Modern Approaches to Culture of Preimplantation Mammalian Embryos In Vitro. Russian Journal of Developmental Biology 45(2): 73-88; English abstract on p. 88.

Buehrer and Reitemeier (1940) The Inhibiting Action of Minute Amounts of Sodium Hexametaphosphate on the Precipitation of Calcium Carbonate from Ammoniacal Solutions. II. Mechanism of the Process, with Special Reference to the Formation of Calcium Carbonate Crystals. The Journal of Physical Chemistry 44(5): 552-574.

Bursac et al., (2015) Synergizing Engineering and Biology to Treat and Model Skeletal Muscle Injury and Disease. Annu Rev Biomed Eng 17: 217-242.

Caglar Aytac et al., (2015) Can calcium ionophore "use" in patients with diminished ovarian reserve increase fertilization and pregnancy rates? A randomized, controlled study. Fertil Steril 104(5): 1168-1174.

Cairns (2006) Lactic acid and exercise performance : culprit or friend? Sports Med 36(4): 279-291.

Campbell et al., (2012) Models of bone metastasis. J Vis Exp 67: e4260; 7 pages.

Chen et al., (2013) Ethanol assisted synthesis of pure and stable amorphous calcium carbonate nanoparticles. Chemical Communications 49(83): 9564-9566.

Chick and Borah (1990) Calcium carbonate gel therapy for hydrofluoric acid burns of the hand. Plast Reconstr Surg 86(5): 935-940.

Clarkson et al., (1992) Role of metastable phases in the spontaneous precipitation of calcium carbonate. Journal of the Chemical Society. Faraday Transactions 88(2): 243-249.

Culligan and Ohlendieck (2002) Abnormal Calcium Handling in Muscular Dystrophy. Basic Appl Myol 12(4): 147-157.

Datta et al., (2015) Add-ons in IVF programme—Hype or Hope? Facts Views Vis Obgyn 7(4): 241-250.

Delaporte et al., (1986) Human myotube differentiation in vitro in different culture conditions. Biol Cell 57(1): 17-22. Abstract.

Doki et al., (1999) Mediastinal lymph node metastasis model by orthotopic intrapulmonary implantation of Lewis lung carcinoma cells in mice. Br J Cancer 79(7-8): 1121-1126.

Eftekhar et al., (2013) Effect of oocyte activation with calcium ionophore on ICSI outcomes in teratospermia: A randomized clinical trial. Iran J Reprod Med 11(11): 875-882.

Faes and Dormond (2015) Systemic Buffers in Cancer Therapy: The Example of Sodium Bicarbonate; Stupid Idea or Wise Remedy? Med chem 5(12): 540-544.

Fleetham et al., (1993) The mouse embryo culture system: improving the sensitivity for use as a quality control assay for human in vitro fertilization. Fertil Steril 59(1): 192-196.

Flinck et al., (2018) Roles of pH in control of cell proliferation. Acta Physiol (Oxf) 223(3): e13068; 17 pages.

Fujita, "Osteoporosis drugs" Chiryo 72: 455-459, 1990.

Gal et al., (1996) Calcium carbonate solubility: a reappraisal of scale formation and inhibition. Talanta 43(9): 1497-1509.

Glacken et al., (1986) Reduction of waste product excretion via nutrient control: Possible strategies for maximizing product and cell yields on serum in cultures of mammalian cells. Biotechnol Bioeng 28(9): 1376-1389.

Glimcher (1984) Recent studies of the mineral phase in bone and its possible linkage to the organic matrix by protein-bound phosphate bonds. Philos Trans R Soc Lond B Biol Sci 304(1121): 479-508.

Hall et al., (2016) Lactate: Friend or Foe. PM R 8(3 Suppl): S8-S15.

Halloran and Donachy (1995) Characterization of organic matrix macromolecules from the shells of the Antarctic scallop, Adamussium colbecki. Comp Biochem Physiol B Biochem Mol Biol 111(2): 221-231.

Hecker et al., (2003) Phosphorylation of serine residues is fundamental for the calcium-binding ability of Orchestin, a soluble matrix protein from crustacean calcium storage structures. FEBS Lett 535(1-3): 49-54.

(56) References Cited

OTHER PUBLICATIONS

Hentemann et al., (2011) Differential pH in embryo culture. Fertil Steril 95(4): 1291-1294.
Hu et al., (2004) Effect of calcium supplements on osteoporosis by using nuclear analytical techniques. J Radioanalytical & Nuclear Chemistry 259: 369-373.
Hu et al., (2010) Strongly bound citrate stabilizes the apatite nanocrystals in bone. Proc Natl Acad Sci USA 107(52): 22425-22429.
Huang et al., (2007) A carbonate controlled-addition method for amorphous calcium carbonate spheres stabilized by poly (acrylic acid) s. Langmuir 23(24): 12086-12095.
Huxley, "The natural history of the common crayfish" in The Crayfish: An Introduction to the Study of Zoology, Chapter 1, pp. 1-45 and reprinted as 20 HTML sheets, 1879.
Ihli et al., (2013) Freeze-drying yields stable and pure amorphous calcium carbonate (ACC). Chem Commun 49: 3134-3136.
Inoue et al., (2001) Purification and structural determination of a phosphorylated peptide with anti-calcification and chitin-binding activities in the exoskeleton of the crayfish, Procambarus clarkii. Biosci Biotechnol Biochem 65(8): 1840-1848.
Inoue et al., (2007) Significance of the N-and C-terminal regions of CAP-1, a cuticle calcification-associated peptide from the exoskeleton of the crayfish, for calcification. Peptides 28(3): 566-573.
Ishii et al., (1998) Solubilization and Chemical Characterization of an Insoluble Matrix Protein in the Gastroliths of a Crayfish, Procambarus clarkii, Biosci Biotechnol Biochem, vol. 62(2): 291-296 4 pages.
J.D. "Oculi cancrorum: Very proper for falls and a pleurisy" Annals of the Royal College of Surgeons of England, 20: 57-58, 1957.
Johnsson et al., (1991) Adsorption and mineralization effects of citrate and phosphocitrate on hydroxyapatite. Calcif Tissue Int 49(2): 134-137.
Joyce et al., (2012) Bone health and associated metabolic complications in neuromuscular diseases. Phys Med Rehabil Clin N Am 23(4): 773-799.
Kavanagh et al., (1990) Inhibitor effects on calcite growth at low supersaturations. Journal of the Chemical Society, Faraday Transactions 86(6): 965-972.
Kevenaar and Hoogenraad (2015) The axonal cytoskeleton: from organization to function. Front Mol Neurosci 8: 44; 12 pages.
Kojima et al., (1993) Synthesis of Amorphous Calcium Carbonate and Its Crystallization. Journal of Ceramic Society of Japan 101(10): 1145-1152. Abstract.
Komuro (1996) Treatment manual for renal disease VIII. 313. Calcium preparations. Kidney and Dialysis Special Edition 41: 871-872 English translation.
Kumar and Singh (2015) Trends of male factor infertility, an important cause of infertility: A review of literature. J Hum Reprod Sci 8(4): 191-196.
Lamb et al., (2006) Point: Counterpoint: Lactic acid accumulation is an advantage/disadvantage during muscle activity J Appl Physiol 100: 1410-1414.
Lee et al., (2005) Fabrication of unusually stable amorphous calcium carbonate in an ethanol medium. Materials Chemistry and Physics 93(2-3): 376-382.
Lin and Singer (2005) Inhibition of calcite crystal growth by polyphosphates. Water Research 39(19): 4835-4843.
Lin et al., (2015) Effects of Chalk Use on Dust Exposure and Classroom Air Quality. Aerosol and Air quality research 15: 2596-2608.
Loste et al., (2003) The role of magnesium in stabilising amorphous calcium carbonate and controlling calcite morphologies. Journal of Crystal Growth 254(1-2): 206-218.
Lopes-Silva et al., (2018) Acute and chronic effect of sodium bicarbonate ingestion on Wingate test performance: a systematic review and meta-analysis. Journal of Sports Sciences, DOI: 10.1080/02640414.2018.1524739; 11 pages.
Luquet and Marin (2004) Biomineralisations in crustaceans: storage strategies. Comptes Rendus Palevol 3(6-7): 515-534.
Lynch and Cate (2005) The anti-caries efficacy of calcium carbonate-based fluoride toothpastes. Int Dent J 55(3 Suppl 1): 175-178.
Ma et al., (2007) A novel extrapallial fluid protein controls the morphology of nacre lamellae in the pearl oyster, Pinctada fucata. J Biol Chem 282(32): 23253-23263.
Malkaj and Dalas (2007) The effect of acetaminophen on the crystal growth of calcium carbonate. J Mater Sci Mater Med 18(5): 871-875.
Manoli and dalas (2002) The effect of sodium alginate on the crystal growth of calcium carbonate. J Mater Sci Mater Med 13(2): 155-158.
Manor et al., (2002) Intensification of redclaw crayfish Cherax quadricarinalus culture II. Growout in a separate cell system. Aquacultural Engineering 26: 263-276.
Marín-Briggiler et al., (2003) Calcium requirements for human sperm function in vitro. Fertil Steril 79(6): 1396-1403.
Martins et al., (2008) Hydroxyapatite micro-and nanoparticles: nucleation and growth mechanisms in the presence of citrate species. J Colloid Interface Sci 318(2): 210-216.
Maruyama et al., (2011) Synthesizing a composite material of amorphous calcium carbonate and aspartic acid. Materials Letters 65(2): 179-181.
Meiron et al., (2011) Solubility and bioavailability of stabilized amorphous calcium carbonate. J Bone Miner Res 26(2): 364-372.
Michl et al., (2019) Evidence-based guidelines for controlling pH in mammalian live-cell culture systems. Commun Biol 2: 144; 12 pages.
Müller et al., (2015) Nonenzymatic Transformation of Amorphous CaCO3 into Calcium Phosphate Mineral after Exposure to Sodium Phosphate in Vitro: Implications for in Vivo Hydroxyapatite Bone Formation. ChemBioChem 16(9):1323-1332.
Multigner et al., (1983) Pancreatic stone protein, a phosphoprotein which inhibits calcium carbonate precipitation from human pancreatic juice. Biochemical And Biophysical Research Communications 110(1): 69-74.
Naciri et al., (2008) Monitoring pH and dissolved oxygen in mammalian cell culture using optical sensors. Cytotechnology 57(3): 245-250.
Nagasawa and Ishii (1996) The chemical structure of insoluble organic matrix contained in Procambarus clarkia gastrolith. Kaiyo Monthly 28: 688-693 English translation.
Nakatsuji et al., (2000) Changes in the Amounts of the Molt-Inhibiting Hormone in Sinus Glands during the Molt Cycle of the American Crayfish, Procambarus clarkii. Zoolog Sci 17(8): 1129-1136.
Nasiri and Eftekhari-Yazdi (2015) An overview of the available methods for morphological scoring of pre-implantation embryos in in vitro fertilization. Cell J 16(4): 392-405.
Nebel et al., (2008) On the structure of amorphous calcium carbonate—A detailed study by solid-state NMR spectroscopy. Inorganic Chemistry 47(17): 7874-7879.
Ogino et al., (1988) Effect of polyamine-n-polyphosphonic acid on the formation and the transformation of calcium-carbonate. Nippon Kagaku Kaishi (6): 899-905.
Parnes and Sagi (2002) Intensification of redclaw crayfish Cherax quadricarinalus culture I. Hatchery and nursery system. Aquacultural Engineering 26: 251-262.
Pfeifer et al., (2002) Vitamin D and muscle function. Osteoporos Int 13(3): 187-194.
Pfeifer et al., (2009) Effects of a long-term vitamin D and calcium supplementation on falls and parameters of muscle function in community-dwelling older individuals. Osteoporos Int 20: 315-322.
Pilon-Thomas et al., (2016) Neutralization of Tumor Acidity Improves Antitumor Responses to Immunotherapy. Cancer Res 76(6): 1381-1390.
Pradhan et al., (2012) In situ pH maintenance for mammalian cell cultures in shake flasks and tissue culture flasks. Biotechnol Prog 28(6): 1605-1610.
Qi et al., (2014) Atp-stabilized amorphous calcium carbonate nanospheres and their application in protein adsorption. Small 10(10): 2047-2056.

(56) References Cited

OTHER PUBLICATIONS

Raz et al., (2002) Stable amorphous calcium carbonate is the main component of the calcium storage structures of the crustacean Orchestia cavimana. Biol Bull 203: 269-274.
Reddi et al., (1980) Influence of phosphocitrate, a potent inhibitor of hydroxyapatite crystal growth, on mineralization of cartilage and bone. Biochem Biophys Res Commun 97(1): 154-159.
Rahman et al., (2014) Calcium influx and male fertility in the context of the sperm proteome: an update. Biomed Res Int 2014: 841615; 13 pages.
Requena et al., (2005) Sodium bicarbonate and sodium citrate: ergogenic aids? J Strength Cond Res 19(1): 213-224.
Robey et al., (2009) Bicarbonate increases tumor pH and inhibits spontaneous metastases. Cancer Res 69(6): 2260-2268.
Rodriguez-Blanco et al., (2008) How to make 'stable'ACC: protocol and preliminary structural characterization. Mineralogical Magazine 72(1): 283-286.
Rodriguez-Blanco et al., (2012) The role of pH and Mg on the stability and crystallization of amorphous calcium carbonate. Journal of Alloys and Compounds 536(Supp 1): S477-S479 International Symposium on Metastable, Amorphous and Nanostructured Materials, ISMANAM-2011 (Jun. 26 to Jul. 1, 2011).
Rossi et al., (2019) Calcium, mitochondria and cell metabolism: A functional triangle in bioenergetics. Biochim Biophys Acta Mol Cell Res 1866(7): 1068-1078.
Saitoh et al., (1985) Inhibition of calcium-carbonate precipitation by human salivary proline-rich phosphoproteins. Arch Oral Biol 30(8): 641-643.
Saunders et al., (2017) β-alanine supplementation to improve exercise capacity and performance: a systematic review and meta-analysis. Br J Sports Med 51(8): 658-669.
Sawada (1997) The mechanisms of crystallization and transformation of calcium carbonates. Pure and Applied Chemistry 69(5): 921-928.
Sawada et al., (2003) Adsorption of inorganic phosphates and organic polyphosphonate on calcite. Dalton Trans 2003 (3): 342-347.
Schepers (1959) Pulmonary histologic reactions to inhaled fiberglas-plastic dust. The American Journal of Pathology 35(6): 1169-1187.
Sfontouris et al., (2015) Artificial oocyte activation to improve reproductive outcomes in women with previous fertilization failure: a systematic review and meta-analysis of RCTs. Hum Reprod 30(8): 1831-1841.
Shaltiel et al., (2013) Bone loss prevention in ovariectomized rats using stable amorphous calcium carbonate. Health 5 (7A2): 18-29.
Shechter et al., (2008) A gastrolith protein serving a dual role in the formation of an amorphous mineral containing extracellular matrix. Proc Natl Acad Sci U S A 105(20): 7129-7134.
Shin et al., (2013) Wasting mechanisms in muscular dystrophy. Int J Biochem Cell Biol 45(10): 2266-2279.
Schneiders et al., (2007) Effect of modification of hydroxyapatite/collagen composites with sodium citrate, phosphoserine, phosphoserine/RGD-peptide and calcium carbonate on bone remodelling. Bone 40(4): 1048-1059.
Shian et al., (1997) Effect of commercial fortified calcium products on calcium status in rats. Acta Nutrimenta Sinica Abstract.
Spiegel et al., (1983) Group therapy and hypnosis reduce metastatic breast carcinoma pain. Psychosomatic Medicine 45(4): 333-339.
Sugawara et al., (2006) Self-organization of oriented calcium carbonate/polymer composites: Effects of a matrix peptide isolated from the exoskeleton of a crayfish. Angew Chem Int Ed Engl 45(18): 2876-2879.
Sugawara et al., (2006) Supporting information. Angewandte Chemie International Edition 45(18): S1-S5.
Takagi et al., (2000) Immunolocalization of gastrolith matrix protein (GAMP) in the gastroliths and exoskeleton of crayfish, Procambarus clarkii. Zoological Science 17: 179-184.
Tanner et al., (2010) Evaluation of three portable blood lactate analysers: Lactate Pro, Lactate Scout and Lactate Plus. Eur J Appl Physiol 109(3): 551-559.

Thomas and Birchall (1983) The retarding action of sugars on cement hydration. Cement and Concrete Research 13(6): 830-842.
Thys-Jacobs et al., (1998) Calcium carbonate and the premenstrual syndrome: Effects on premenstrual and menstrual symptoms. American Journal of Obstetrics and Gynecology 179(2):444-452.
Tlili et al., (2002) Characterization of CaCO3 hydrates by micro-Raman spectroscopy. Journal of Raman Spectroscopy 33(1): 10-16.
Tobias et al., (2013) Additive effects of beta-alanine and sodium bicarbonate on upper-body intermittent performance. Amino Acids 45(2): 309-317.
Todd (2014) Lactate: valuable for physical performance and maintenance of brain function during exercise. Bioscience Horizons: The International Journal of Student Research 7: hzu001.
Tolba et al., (2016) High biocompatibility and improved osteogenic potential of amorphous calcium carbonate/vaterite. Journal of Materials Chemistry B 4(3): 376-386.
Travis (1960) The Deposition of Skeletal Structures in the Crustacea. I. The Histology of the Gastrolith Skeletal Tissue Complex and the Gastrolith in the Crayfish, Orconectes (Cambarus) Virllis Hagen—Decapoda. Biol Bull 118: 137-149.
Travis (1963) Structural features of mineralization from tissue to macromolecular levels of organization in the decapod Crustacea. Ann N Y Acad Sci 109: 177-245.
Tsutsui et al., (1999) Cloning and expression of a cDNA encoding an insoluble matrix protein in the gastroliths of a crayfish, Procambarus clarkia. Zoological Science (Tokyo) 16(4): 619-628.
Ueno and Mizuhira (1984) Calcium transport mechanism in crayfish gastrolith epithelium correlated with the molting cycle. II. Cytochemical demonstration of Ca2+-ATPase and Mg2+-ATPase. Histochemistry 80(3): 213-217.
Väisänen, (2011) CaCO3 scale inhibition in paper making processes—evaluation of testing methods and inhibitor performance. Master of science thesis, 1-95.
Vaisman et al., (2014) Increased calcium absorption from synthetic stable amorphous calcium carbonate: double-blind randomized crossover clinical trial in postmenopausal women. J Bone Miner Res 29(10): 2203-2209.
van der Valk et al., (2010) Optimization of chemically defined cell culture media—replacing fetal bovine serum in mammalian in vitro methods. Toxicol In Vitro 24(4): 1053-1063.
Verbitsky et al., (1997) Effect of ingested sodium bicarbonate on muscle force, fatigue, and recovery. J Appl Physiol (1985) 83(2): 333-337.
Wagner et al., (2007) Current treatment of adult Duchenne muscular dystrophy. Biochim Biophys Acta 1772(2): 229-237.
Wan et al., (1989) Regulation of citric acid cycle by calcium. J Biol Chem 264(23): 13430-13439.
Warburg (1956) On the origin of cancer cells. Science 123(3191): 309-314.
Weinstein et al., (1998) Reliability of peak-lactate, heart rate, and plasma volume following the Wingate test. Med Sci Sports Exerc 30(9): 1456-1460. Retrieved from: https://journals.lww.com/acsm-msse/Fulltext/1998/09000/Reliability_of_peak_lactate,_heart_rate,_and.17.aspx on Apr. 27, 2022. 11 pages.
Westerblad et al., (2002) Muscle fatigue: lactic acid or inorganic phosphate the major cause? News Physiol Sci 17: 17-21.
Williams et al., (2015) Mitochondrial calcium and the regulation of metabolism in the heart. J Mol Cell Cardiol. Author manuscript; available in PMC May 25, 2019. Published in final edited form as: J Mol Cell Cardiol. Jan. 2015; 78: 35-45.
Withnall (2000) Biology of Yabbies (cherax destructor), Aquaculture Information Notes, Department of Primary Industries, 6 pages.
Wolf and Günther (2001) Thermophysical investigations of the polymorphous phases of calcium carbonate. Journal of Thermal Analysis and Calorimetry 65(3): 687-698.
Xu et al., (2005) Stable amorphous CaCO3 microparticles with hollow spherical superstructures stabilized by phytic acid. Advanced Materials 17(18): 2217-2221.
Xurong et al., (2008) Amorphous Calcium Carbonate in Biomineralization. Progress in Chemistry 20(1): 54-59.
Yudkovsky (2007) Hepatopancreatic multi-transcript expression patterns in the crayfish Cherax quadricarinatus during the moult cycle. Insect Molecular Biology 16(6): 661-674.

(56) References Cited

OTHER PUBLICATIONS

Zajac et al., (2009) Effects of sodium bicarbonate ingestion on swim performance in youth athletes. J Sports Sci Med 8(1): 45-50.
Agilent Seahorse XF Cell Mito Stress Test Kit. User Guide Kit 103015-100. Agilent Technologies. Printed in USA, May 2019, Revision G0 Retrieved from: http://www.agilent.com/cs/library/usermanuals/Public/XF_Cell_Mito_Stress_Test_Kit_User_Guide.pdf on Apr. 27, 2022. 20 pages.
amorphous calcium carbonate. NIH; National Cancer Institute. Retrieved from: https://www.cancer.gov/publications/ dictionaries/cancer-drug/def/amorphous-calcium-carbonate?redirect=true, on Aug. 6, 2021. 1 page.
"Animal Reproduction Biotechnology", Sang Yun Zi editor. China Agriculture Press, Jul. 31, 2006. pp. 343-344. Machine translation.
Calcium in Cell Culture; Importance and uses of calcium in serum-free eucaryotic, including hybridoma and Chinese Hamster Ovary (CHO) cell cultures. Sigma-Aldrich. Retrieved from: https://web.archive.org/web/20150524020552/ https:/www.sigmaaldrich.com/life-science/cell-culture/learning-center/media-expert/calcium.html May 24, 2015. 2 pages.
Clinical Orthopedic Complications, 1st Edition, Edited by: Qiu Rucheng, p. 139, China Medical Science and Technology Press, Dec. 31, 2007. With machine translation.
Database Uniprot P98157 (1996) Internet site http://www.uniprot.org/uniprot/P98157.html—last modified Nov. 30, 2010—22 pages.
Database WPI Week 200432 Thomson Scientific, London, GB; AN 343036 XP002512142 & JP 2004 081739 A (Bankoku Needle MFG) Mar. 18, 2004 (Mar. 18, 2004) & JP 2004 081739 A (Akashi Mitsuru; Tabata Masashi; Biomedical Technology Hybrid L) Mar. 18, 2004 (Mar. 18, 2004).
DMD_M.2.1.005 (SOP (ID) Number): "The use of four limb hanging tests to monitor muscle strength and condition over time"; George Carlson (Author), Maaike van Putten (Official reviewer). Issued: Aug. 3, 2011 and Last reviewed: Jun. 29, 2016; 11 pages.
Duchenne Diagnosis of Bone and Joint Disorders. Edited by Resnick D; 4th edition, 2009. Elsevier (Singapore) Pte Ltd.; p. 3595. With machine translation; 3 pages.
GenCore Database, (2012) DQ847548. 3 pages.
Hypocalcemia; Section 12: Endocrine and Metabolic Disorders. In: The Merck Manual of Diagnosis and Therapy, 18th edition. Mark H. Beers (Editor-in-Chief), Robert S. Porter (Editor), Thomas V. Jones (Associate Editor), Justin L. Kaplan (Senior Assistant Editor) and Michael Berkwits (Assistant Editor). Merck Research Laboratories, Division of Merck & Co., Inc.; Whitehouse Station, NJ; 2006, pp. 1250-1254. And Merck Manual 18th Edition Japanese Edition, 2006, pp. 1319-1323.
Melanoma skin cancer (2013) American Cancer Society. 3 pages.
Merck manual of diagnosis and therapy 17th edition 1999 pp. 1979, 1982.
Neuronal Synaptic Transmission Cells and Molecular Biology (Neurobiology). Edited by Zuhang S, 2008. Shanghai Science and Technology Press; p. 69. With machine translation; 3 pages.

Non-Hodgkin lymphoma, (2012) American Cancer Society. 5 pages.
Occupational Safety and Health Administration (OSHA), 1995; Occupational Safety and Health Guideline for Calcium Carbonate. U.S. Department of Health and Human Services and U.S. Department of Labor; 7 pages.
Osteoporosis (2005) How to strengthen your bones and prevent fractures. The healthier Life. 3 pages.
Osteophase, (2011) Tango advanced Nutrition—Healthy Bone Support Formula. 3 pages.
Pathology. Edited by Enhua W, 2003. Higher Education Press, Beijing, China; p. 307. With machine translation; 4 pages.
Stoelting's Anesthesia and Co-Existing Disease. Edited by Hines RL and Marschall K, 2012. Elsevier (Singapore) Pte Ltd.; p. 420. With machine translation; 3 pages.
"Testing the Effect of Crustacean's Gastrolith Nutraceutical on Mineralization Rate During Distraction Osteogenesis"; Amorfical (Collaborator), Ron Lamdan, Hadassah Medical Organization (Responsible Party). Study NCT01087437, last updated Mar. 30, 2014 (v6). Retrieved from https://clinicaltrials.gov/ct2/history/NCT01087437?V_6=View#StudyPageTop on Jan. 24, 2019; 4 pages.
The Merck Manual of Diagnosis and Therapy. Edited by Beers MH and Berkow R. 17th Edition, 1999. Published by Merck Research Laboratories, division of Merck & Co., Inc., White house Station, NJ, USA. 3 pages.
Aljaloud (2015) Dietary supplements for professional athletes: a great potential for Saudi Arabia. J Nutr Health Food Eng 3(1): 272-277.
Coleman Ellen, Eating for Endurance, fourth edition. Per. from English—Murmansk: Tuloma Publishing House, 2005. pp. 62-64. Machine translation.
Hassan and Lau (2009) Effect of particle shape on dry particle inhalation: study of flowability, aerosolization, and deposition properties. AAPS PharmSciTech 10(4): 1252-1262.
Shete et al., (2015) Formulation of Eco-friendly Medicated Chewing Gum to Prevent Motion Sickness. AAPS PharmSciTech 16(5): 1041-1050.
Zhang Haichao (1994) Calcium Effects on Organ Capacity of Sports. Journal of Shanxi Teacher's University, Natural Science Edition 8(4): 55-58. Abstract on p. 58.
Zhao Jing-guo (2001) Cytobiological Mechanisms of Muscle Fatigue and Correlative Prevention and Cure Measures. Shandong Sports Science & Technology 23(1): 26-29. Abstract.
Zhulenko V.N., Gorshkov G.I.; Pharmacology. Textbooks and Tutorials for Higher Educational Institutions Students. Moscow "Kolos" 2008, pp. 34-35. Machine translation.
Community Medication Manual. Yaohua Zhang et al., Shanghai Jiao Tong University Press, Dec. 31, 2008. p. 369. Machine translation.
Database GNPD [Online] MINTEL; Oct. 24, 2018 (Oct. 24, 2018), anonymous: "d-nox Muscle Pump Mineral and Vitamin Supplement", XP093053163, Database accession No. 6073225.
One Hundred Thousand Whys, Volume in Human Body Science, universal edition published by New Century, by Binghui Yang, p. 68, Shanghai: Juvenile & Children's Publishing House. Aug. 31, 2003. Machine translation.

La Profile

AMORPHOUS CALCIUM CARBONATE FOR IMPROVING ATHLETIC PERFORMANCE

FIELD OF THE INVENTION

The present invention provides compositions comprising stabilized amorphous calcium carbonate as a means for improving athletic performance, such as improving aerobic and anaerobic performance, improving muscle performance, enhancing muscle strength and endurance, and reducing muscle fatigue and time to recovery.

BACKGROUND OF THE INVENTION

Most athletes, whether professional or recreational, are driven to achieve peak, or at least an increased, athletic performance. This drive is predicated by the desire for self-improvement. Most recreational and professional athletes achieve these goals through a prolonged exercise to improve their athletic performance coupled with proper diet and supplements.

Muscle performance is a general term used to define the collectively muscle power strength and endurance. Muscle fatigue is a common symptom during sport and exercise activities but is also increasingly observed as a secondary outcome in many diseases and health conditions during the performance of everyday activities. Muscle fatigue is often defined as a reversible decline of force production during activity. Muscle fatigue consists of a complex interplay between central and peripheral fatigue. The extent of peripheral muscle fatigue is dependent on several factors.

The most common way to increase muscle performance is training, such as strength training or endurance training. However, this approach is not always sufficient. In such cases, pharmacological treatment, nutritional supplementation, or, sometimes, physical impact such as electrostimulation is used.

US 2015/0250784 describes improving resistance to skeletal muscle fatigue by administering to a person a skeletal muscle troponin activator.

U.S. Pat. No. 9,192,601 describes methods for promoting muscle tone mass or endurance by administering compositions comprising AMPK agonists.

WO 2008/041236 describes treating musculoskeletal disorders by compositions comprising calcium carbonate ($CaCO_3$) finely mixed with an organic matter essentially consisting of chitin and polypeptide (Pp), wherein said specific ratios between $CaCO_3$ and organic matter or said polypeptide is indicated.

WO 2013/088440 disclosed that the bioavailability of amorphous calcium carbonate was significantly higher than the bioavailability of crystalline calcium carbonate. Meiron (Journal of Bone and Mineral Research, Vol. 26, No. 2, 2011, pp 364-372) reached a similar observation and further stated that the amorphous calcium carbonate is approximately 120 times more soluble than calcite (one of the crystalline forms of calcium carbonate).

Verbitsky et al., (Journal of Applied Physiology, 1997, 83 (2), 333-337) tested the influence of acute ingestion of $NaHCO_3$ on fatigue and recovery of the quadriceps femoris muscle after exercise in six healthy male subjects. As cited in Verbitsky, although previously published work of the effect of $NaHCO_3$ on anaerobic performance shows variable results, there was an agreement that $NaHCO_3$ ingestion of at least 300 mg/kg body mass prolongs high-intensity exercise. Based on the results of the conducted experiments Verbitsky concluded that acute ingestion of 400 mg/kg of $NaHCO_3$ is an effective means for increasing the torques in an isometric contraction, thus reducing muscle fatigue and enhancing recovery.

Zajac et al., (Journal of Sports Science and Medicine (2009) 8, 45-50) showed that oral administration of 300 mg/kg of sodium bicarbonate can increase training intensity and swimming performance.

Requena et al., (Journal of Strength and Conditioning Research, 2005, 19(1), 213-224) reviewed several studies examining the influence of administration of sodium bicarbonate and sodium citrate on human performance. Interestingly, it was shown that when different doses were tested, the significant effect was shown only for doses above 300 mg/kg for sodium bicarbonate. Requena et al. concluded that benefits from the exogenous ingestion of $NaHCO_3$ and Na-citrate are obtained in activities with a duration sufficient to generate a difference in the $H^+$ ion gradient. These activities are very high intensity, recruit fast motor units, and involve large muscle groups.

Lopes-Silva et al (Journal of Sports Sciences, DOI: 10.1080/02640414.2018.1524739) performed a systematic review and meta-analysis on the acute and chronic effects of sodium bicarbonate ($NaHCO_3$) ingestion on Wingate performance. Results of the meta-analysis showed that acute ingestion of $NaHCO_3$ did not improve Wingate test peak or mean power even with high dosage, whereas the chronic ingestion of $NaHCO_3$ did. However, to achieve the improvement the subject had to administer between 300 to 500 mg/kg of $NaHCO_3$.

These studies implied that sodium bicarbonate may be useful for improving athletic performances. However, to get the improvement, the athlete had to administer about 20-35 g/day of $NaHCO_3$, an enormous amount for a daily supplement, that contains several folds of the maximum sodium recommended per day by health authorities. Athletes taking these levels of $NaHCO_3$ have reported adverse effects such as stomach aches and discomfort, nausea, and vomiting.

In a recent meta-analysis review article by Sounders et al (2016), Sounders found that β-alanine supplementation has a significant overall ergogenic effect on exercise. Exercise duration is the greatest influencing factor in the efficacy of β-alanine supplementation. The co-supplementation of β-alanine and sodium bicarbonate resulted in the largest effect sizes, and also resulted in greater gains than β-alanine alone, though the gain seems to be an additive one and not synergistic. There were no conclusions regarding endurance and performance for long periods of activities such as for long-distance runners and swimmers and game players.

There is an unmet need for developing and finding safe and effective means for improving athletic performance and specifically of athletes and subsequently enhancing athletic achievements.

SUMMARY OF THE INVENTION

The present invention is based on the surprising finding that the administration of calcium carbonate, which is considered as a poorly soluble substance, can efficiently improve athletic performance. In particular, it is now shown that stabilized amorphous calcium carbonate (ACC) may efficiently increase muscle power, decrease muscle fatigue and therefore improve muscle performance and in general improved athletic performance of people engaged in intense physical activities, especially professional athletes. In one aspect, the present invention provides a method of improving an athletic performance of a subject comprising administering to said subject a composition comprising amorphous calcium carbonate (ACC) stabilized by at least one stabilizer. In another aspect, the present invention provides a non-therapeutic use of a composition comprising amorphous calcium carbonate (ACC) stabilized by at least one stabilizer in improving an athletic performance of a subject. According to another aspect, the present invention provides a composition comprising amorphous calcium carbonate (ACC) stabilized by at least one stabilizer for non-therapeutic use in improving athletic performance of a subject.

According to any one of the aspects of the present invention, improving athletic performance comprises improving at least one of the endurance, strength, and recovery from physical activity of a subject. According to some embodiments, improving of athletic performance comprises elongating the duration of physical activities, performing it faster, or both. According to some embodiments, improving athletic performance comprises improving muscle performance. According to some embodiments, improving muscle performance comprises improving at least one of muscle strength, muscle endurance, muscle recovery, reducing muscle fatigue and/or increasing muscle power. According to some embodiments, improving muscle performance improves the athletic performance of a subject. According to any one of the above embodiments, administering comprises administering of 30 to 200 mg/kg/day of stable ACC. According to some embodiments, administering comprises administration of 3000 to 10000 mg/day of ACC. The composition may be administered as one dose or as several divided doses. According to any one of the above embodiments, the composition is formulated as a food supplement that may be in the form of powder, suspension, tablets, or capsules.

According to some embodiments, the subject that may use the composition of the present invention is an athlete, such as a professional and non-professional athlete.

According to any one of the above embodiments, the administration of stabilized ACC is performed by a route selected from sublingual, oral, and both sublingual and oral administration.

The composition of the present invention comprises ACC stabilized by at least one stabilizer. According to some embodiments, the stabilizer is selected from the group consisting of organic acids, phosphorylated, phosphonated, sulfated or sulfonated organic compound, phosphoric or sulfuric esters of hydroxy carboxylic acids, phosphorylated amino acids, bisphosphonate, organic polyphosphate, hydroxyl bearing organic compounds, derivatives thereof, proteins and any combinations thereof.

DETAILED DESCRIPTION OF THE INVENTION

Figure 1:
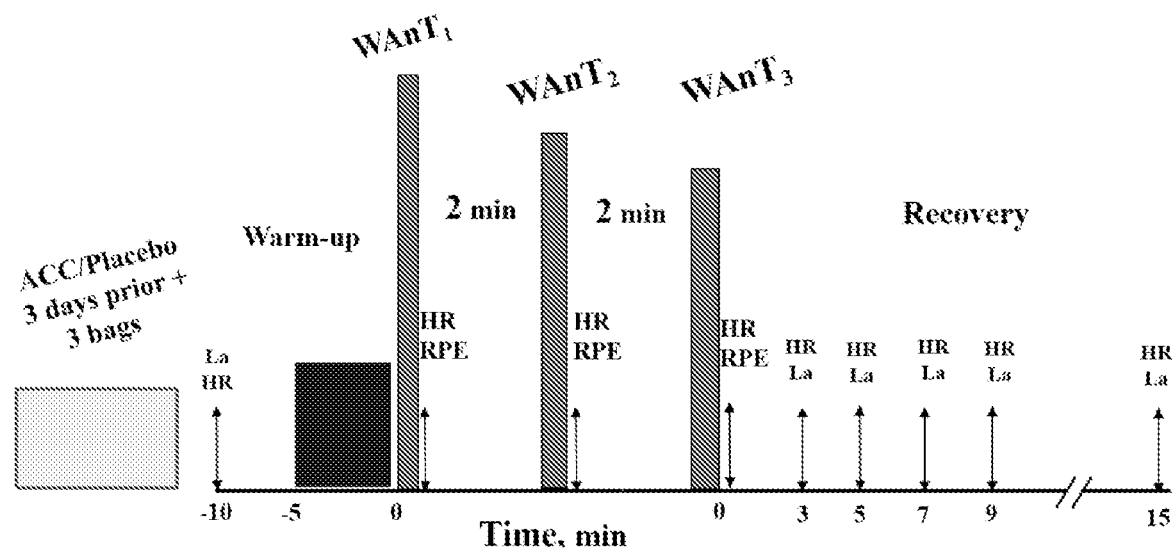
FIG. 1 illustrates the protocol design of a Wingate test performed for each subject and measurements taken. (WAnT—Wingate test, HR—Heart rates, RPE—Rate of perceived exertion, La-Lactate).

It was unexpectedly found according to the teaching of the present invention that stable amorphous calcium carbonate (ACC) may significantly improve the performance of athletes and bring them to better achievements. It was previously shown by the applicant that stable ACC has therapeutic properties in many pathological conditions such as osteoporosis, pain, bone injuries, and even cancer. It was now surprisingly found that stable ACC may help healthy people to improve their athletic performances.

The proof of concept was made on highly professional athletes, for whom it is most difficult to improve performance. The idea behind selecting this group is that if ACC improves the results of highly trained athletes, it will definitely be useful for other non-professionals. Professional athletes chronically suffer from different types of inflammations and injuries due to their extreme activities. Thus, it was important to separate the effect of stabilized ACC administered sublingually and/or orally, on their pathological conditions from the potential effect on their athletic performance. Athletes having pathological conditions were first treated for a medical purpose. After the pathological condition was resolved, they continued taking stabilized ACC to assess any further efficacy for their performance. As seen in the Examples, the athletes using ACC were both cured of their previous pathological conditions and soon after improved their achievements. In some cases, they broke their personal records obtained prior to their medical conditions. Example 3 provides a plurality of examples of professional athletes competing in national and international championships that significantly improved their athletic performances and achievements as a result of taking stabilized amorphous calcium carbonate.

In addition, a controlled experiment was performed, which demonstrated that stabilized amorphous calcium carbonate was more effective in enhancing muscle recovery compared to crystalline calcium carbonate that served as the placebo. Thus, ACC can efficiently improve muscle performance and subsequently athletic performance of professional athletes, and even more, in the case of non-professional ones. Previous studies implied that administering of a very large amount of sodium bicarbonate, which contains several folds of maximum recommended dose of sodium and caused significant side effects, may affect athletic performance. However, the required dose is not bearable by most people. The present invention provides a safe, tolerable method for improving athletic performance.

According to one aspect, the present invention provides a method for improving an athletic performance of a subject comprising administering to said subject a composition comprising amorphous calcium carbonate stabilized by at least one stabilizer. According to another aspect, the present invention provides a composition comprising amorphous calcium carbonate (ACC) stabilized by at least one stabilizer for use in improving an athletic performance of a subject. According to some embodiments, the use is a non-therapeutic use. Thus, according to the aspect, the present invention provides a composition comprising amorphous calcium carbonate (ACC) stabilized by at least one stabilizer for a non-therapeutic use in improving an athletic performance of a subject. According to some embodiments, the present invention provides a non-therapeutic use of a composition comprising amorphous calcium carbonate (ACC) stabilized by at least one stabilizer in improving athletic performance of a subject.

The term "non-therapeutic" as used herein is a concept excluding a medical action aimed to treat a disease, medical or psychological condition, which is a method of surgery, treatment or diagnosis for a human.

The terms "subject" or "individual" are used interchangeably and refer to either a human or a non-human animal. These terms include mammals, such as humans, primates, livestock animals (including bovine, porcine, etc.), companion animals (e.g., canines, felines, etc.) and rodents (e.g., mice and rats). According to other embodiments, the subject is an animal such as livestock animals or domestic animals. According to some embodiments, the subject is a human subject. According to one embodiment, the subject is a healthy human subject having normal athletic, muscle, and cardiovascular performance. According to some embodiments, the subject is a human subject. According to some embodiments, the subject is an athlete. Thus, in some embodiments, the present invention provides a composition comprising amorphous calcium carbonate (ACC) stabilized by at least one stabilizer for a non-therapeutic use in improving an athletic performance of an athlete.

According to the invention, the terms "athlete" and "sportsman" are used herein interchangeably and refer to a person (men or women) performing exercises for training, maintaining health, general health improvement, and for rehabilitation. The term athlete includes people with beginner, intermediate, and expert levels of experience.

According to one embodiment, the athlete is a professional athlete. The term "professional", "competing sportsmen" or "trained sportsmen" are used herein interchangeably and are taken to mean any person regularly doing physical activity at a professional level, e.g. practicing intense physical activity or sports for at least 3 hours a week for at least two consecutive weeks. The term "professional athlete" encompasses also an athlete that participates in national and international competitions and is daily trained to achieve records at national and international levels. According to some embodiments, the athlete possesses natural or acquired traits, such as strength, agility, and endurance that are necessary for physical exercise or sports, especially those performed in competitive contexts. In some embodiments, the athlete is a non-professional athlete. The terms "non-professional", "amateur" or "non-competing sportsmen" is taken to mean any person sporadically and non-professionally doing physical exercise.

The term "athletic performance" is used herein to generically refer to any type of athletic activity, event, exercise, training, routine, or the like. This is a complex term that relates to at least one of the following: skills, achievements, strength, endurance, speed, power, and recovery of a subject after performing a physical activity, e.g. an intense physical activity.

The terms "improving athletic performance", "enhancing athletic performance" or any lingual variations thereof as used herein should be understood to encompass improvement of at least one sport parameter. Non-limiting examples of such improvements are: testosterone elevation, cortisol reduction, fatigue reduction, faster recovery from exercise, reduced muscle soreness, improved endurance, improved muscle strength, improved muscle size, enhanced athletic performance, improved sports-related decision making, improved selective attention of sports-related stimuli, improved concentration during sports events, and improved mental resilience during sports events. According to some embodiments, improving athletic performance comprises elongating the duration of the physical activities, performing it faster and combination thereof. According to some embodiments, improving athletic performance comprises improving endurance, fatigue reduction, faster recovery and any combination thereof. The terms "improving athletic performance" refers to a change in athletic performance, where the change is defined as a difference in the performance between a subject obtaining the administration according to the invention and a subject in similar conditions or the same subject who does not. In some embodiments, the change is detected or measured on the same subject. The change is regarded as an improvement if such change is positive for said subject. Athletic performance exact definition depends on the type of athletic activity. According to some embodiments, improving athletic performance comprises improving athletic achievements.

The term "physical activity" as used herein, refers to any physical exercise, workout, sports, fitness exercise, and, in general, to any bodily movement. The physical activity may be a short term activity and a prolonged activity.

The term "fatigue reduction" or any lingual variations thereof as used herein should be understood to encompass one or more types of general fatigue reduction such as general physical fatigue, general mental fatigue, heart fatigue, lung fatigue, muscle fatigue, aerobic fatigue, anaerobic fatigue, tiredness, exhaustion, weariness, feeling worn-out, asthenia, lassitude, prostration, exercise intolerance, lack of energy and weakness.

The term "faster recovery" or any lingual variations thereof as used herein should be understood to encompass one or more of general recovery following exercise, muscle recovery, heart and/or lung recovery, recovery of gas concentrations in the blood system, mental recovery, restoration of energy, reduction of physical and mental stress, metabolic recovery, immediate recovery, short-term recovery and training recovery.

The terms "enhanced athletic performance", "improved athletic performance" or any lingual variations thereof as used herein should be understood to encompass one or more of enhanced running endurance, enhanced running speed, enhanced swimming endurance, enhanced swimming speed, enhanced jumping length, enhanced jumping height, enhanced cycling endurance, enhanced cycling speed, enhanced throwing distance, enhanced weightlifting, enhanced rowing endurance, enhanced rowing speed, enhanced walking endurance, enhanced walking speed, enhanced sport's game endurance, and enhanced climbing endurance, and enhanced performance in other similar physical activities.

The term "exercise" as used herein, refers to any form of physical activity. In one embodiment, the exercise enhances or maintains physical fitness. The term "exercise" may refer to strength exercise and endurance exercise. The terms "endurance exercise" and "strength exercise" are well known in the art. Whereas endurance exercise, in particular, aims to increase cardiovascular endurance, strength exercise aims to increase short-term or long-term muscle strength. According to another embodiment, improving athletic performance comprises improving lung performance and endurance. According to another embodiment, improving athletic performance comprises improving of personal records by professional athletes.

According to any aspect of the present invention, improving athletic performance comprises improving at least one of athlete's strength, endurance, recovery, and any combination thereof. According to some embodiment, improving athletic performance comprises improving the subject's athletic achievements. According to some embodiments, improving athletic performance comprises improving the athlete's strength. According to other embodiments, improving athletic performance comprises improving athlete's endurance. According to certain embodiments, improving athletic performance comprises improving athlete's recovery, i.e. reducing the time required for recovery from an exercise. According to one embodiment, improving athletic performance comprises improving aerobic performance. According to another embodiment, improving athletic performance comprises improving cardiovascular performance. According to some embodiments, improving athletic performance comprises improvement anaerobic activity. According to another embodiment, improving athletic performance comprises the improvement of both aerobic and anaerobic activity. According to some embodiments, improving athletic performance comprises the improvement of aerobic capacity and/or aerobic power.

The term "anaerobic exercise" and "anaerobic activity" are used herein interchangeably and refer to exercise that does not increase the body's requirement for oxygen. Typically, anaerobic exercise can be a short-burst, higher-intensity exercise.

The terms "aerobic exercise" and "aerobic activity" refer to exercise that increases the body's requirement for oxygen. Typically, aerobic exercise involves an increased respiratory rate and cardiac rate over an extended period of time. According to any one of the above aspects and embodiments of the present invention, improving athletic performance comprises improving muscle performance. Thus, according to any one of the above aspects and embodiment, the method or the use comprises improving muscle performance. According to some embodiments, improving muscle performance is selected from improving muscle strength, improving muscle endurance, enhancing muscle recovery, increasing muscle power, reducing muscle fatigue, and any combination thereof. According to some embodiments, improving muscle performance comprises reducing muscle pain caused by physical training. According to one embodiment, improving muscle performance comprises improving or enhancing muscle endurance. According to another embodiment, improving muscle performance comprises improving or enhancing muscle recovery. According to some embodiments, improving muscle performance comprises improving or enhancing muscle strength. According to another embodiment, improving muscle performance comprises reducing muscle fatigue. According to one embodiment, improving muscle performance comprises increasing muscle power. According to some embodiments, improving muscle performance comprises improvement of joint mobility. According to other embodiments, improving muscle performance comprises reducing muscle pain, in particular, muscle pain resulted from an exercise or physical activity.

According to any one of the above embodiments, improving muscle performance, e.g. improving muscle strength, improving muscle endurance, enhancing muscle recovery reducing muscle fatigue, increasing muscle power and any combination thereof comprises improving muscle during or following physical activity or exercise.

According to another embodiment, improving muscle performance comprises enhancing energy use by a muscle when performing a physical activity or in rest. According to another embodiment, improving muscle performance comprises increasing muscle cell metabolism. Measurement of cell metabolism may be performed by any known method.

The term "muscle function" as used herein, unless otherwise specified, refers to at least one of muscle mass and muscle strength.

The term "muscle endurance" as used herein refers to the ability of muscle groups to perform submaximal contractions for extended periods of time. Muscle endurance may be measured by any known method, e.g. by measuring a fatigue index calculated for example as the percentage of the differences between the total work during the last 10 repetitions and the first 10 repetitions.

The term "muscle strength" as used herein refers to the amount of force a muscle, or muscle groups in sum, can exert. Muscle strength may be evaluated by a variety of methods such as an isokinetic device in clinical trials such as dynamometer, stationary cycles and treat mill, measuring torque (Nm) and angle (degrees), grip strength, one-repetition maximum strength test, time-dependent tests of muscle endurance, time-dependent tests of muscle fatigue, or time-dependent tests of muscle endurance and fatigue, and so forth. For the maximum strength test, peak torque can be defined as the highest value of torque development in one of several repetitions.

The term "peak power" refers to the greatest output or production of work over a given amount of time. The term "mean power" is the average rate of doing work.

The term "muscle fatigue" or "skeletal muscle fatigue" refers to a reduction in contractile capacity following repeat-use and represents a combination of central fatigue (limitations of the central and peripheral nervous system to sustain activity) and peripheral fatigue (intrinsic loss of muscle function such as reduced effectiveness of excitation-contraction coupling). Muscle fatigue can be assessed by the anaerobic fatigue and anaerobic capacity of a Wingate test. The Wingate test is often performed on a cycle ergometer and consists of a set of time pedaling at maximum speed against a constant force. The number of revolutions pedaled for every five seconds interval during the test is count and is used for determining the power and work data. Anaerobic fatigue demonstrates the percentage of power loss from the beginning to the end of the Wingate test. Anaerobic capacity is the total work completed during the test duration.

The term "muscle recovery" as used herein refers to restoring the muscle condition to its original condition before the exercise or to a better condition. As such, "enhancing muscle recovery" refers to reducing or shortening the time required for muscle recovery. Measurable parameters that can indicate a reduction in muscle recovery time may be the reduction of the lactate levels in the blood along time.

The term "muscle" as used herein refers to skeletal muscles as well as other non-skeletal, striated muscles such as a diaphragm, extraocular muscle, and so forth, and a cardiac muscle. Thus, according to some embodiments, the muscle is selected from the group consisting of skeletal, cardiac, and smooth muscle. According to some embodiments, the present invention provides improving skeletal, cardiac, or smooth muscle performance. According to other embodiments, the present invention provides non-therapeutic use of the composition of the present invention for improving skeletal, cardiac, or smooth muscle performance.

The terms "improving muscle performance" and "enhancing muscle performance" are used herein interchangeably and refer to a change in muscle performance, where the change is defined as a difference in muscle performance between a subject obtaining the treatment or administration according to the invention and a subject in similar conditions who does not. In some embodiments, the change is detected or measured on the same subject. The change is regarded as an improvement if such change is positive for said subject. Normally, an improved muscle performance is an increased muscle performance.

It should be clear that improvement of athletic performance in professional athletes may be small if measured as a percent of change but are significant in their absolute value. According to one embodiment, administering stabilized ACC improves professional athletic performance by about 0.5% to about 10%, about 1% to about 8%, or about 2% to about 6%. Athletic performances may be reflected in any measurable values such as speed (of running or swimming), weight (raised), number of sets performed, distance (a person can jump, run or swim), and time the athlete may keep performing the exercise etc.

The rate of improvement of athletic performance of non-professional athletes may be much more significant. According to some embodiments, administering stabilized ACC enhances improves athletic performance by from about 10% to about 600%, about 20% to about 500%, about 30% to about 400%, about 40% to about 300%, about 50% to about 200%, about 60% to about 150% or about 70% to about 100%. According to some embodiments, administering stabilized ACC improves athletic performance by about 5% to 50%, about 7% to about 40%, about 10% to about 30%, about 15% to about 25% or about 5% to about 20%. According to another embodiment, administering stabilized ACC improves athletic performance by about 10% to about 100%, about 20% to about 90%, about 30% to about 80%, about 40% to about 70%, or about 50% to about 60%. Enhancement by 100% means that the parameter, e.g. muscle strength, improving muscle endurance increased 2 times; enhancement by 200% means that the parameter, is increased 3 times, and so on. According to some embodiments, the athletic performance is improved by about 100% to about 500%, about 120% to about 400%, about 150% to about 300%.

According to one embodiment, administering stabilized ACC enhances muscle performance, such as improving muscle strength, force and/or endurance, by about 10% to about 600%, about 20% to about 500%, about 30% to about 400%, about 40% to about 300%, about 50% to about 200, about 60% to about 150% or about 70% to about 100%. According to some embodiments, administering stabilized ACC enhances muscle performance, such as improving muscle strength, force and/or endurance, by about 5% to 50%, about 7% to about 40%, about 10% to about 30%, about 15% to about 25% or about 5% to about 20%. According to another embodiment, administering stabilized ACC enhances muscle performance, e.g. improving muscle strength, force and/or endurance by about 10% to about 100%, about 20% to about 90%, about 30% to about 80%, about 40% to about 70%, or about 50% to about 60%. Enhancement by 100% means that the parameter, e.g. muscle strength, improving muscle endurance increased 2 times; enhancement by 200% means that the parameter, is increased 3 times, and so on. According to some embodiments, the muscle performance is enhanced by about 100% to about 500%, about 120% to about 400%, about 150% to about 300%. According to some embodiments, enhancing muscle performance comprises reducing muscle fatigue or reducing muscle pain. According to some embodiments, reducing fatigue comprises reducing it by about 5% to about 100%, about 10% to about 90%, about 20% to about 80%, about 30% to about 70% or about 40% to about 60%. Reducing by 100% means completely reducing the feature. According to some embodiments, administering stabilized ACC improves muscle performance of a professional athlete by about 0.5 to about 10%, about 1% to about 8%, or about 2% to about 6%.

According to any one of the above embodiments, the muscle performance refers to muscle performance of a healthy muscle. Thus, according to any one of the above embodiments, the muscle is a healthy muscle, i.e. muscles of a healthy person.

According to one embodiment, the method of the present invention comprises enhancing the athletic performance of athletes, sportsmen or healthy people. According to another embodiment, the method comprises enhancing muscle performance of athletes, sportsmen or healthy people.

According to some embodiments, the present invention provides a composition comprising amorphous calcium carbonate (ACC) stabilized by at least one stabilizer for non-therapeutic use in improving muscle performance of a subject. According to some embodiments, the present invention provides a method for improving muscle performance of a subject comprising administering to said subject a composition comprising amorphous calcium carbonate (ACC) stabilized by at least one stabilizer. According to some embodiments, the present invention provides a non-therapeutic use of a composition comprising amorphous calcium carbonate (ACC) stabilized by at least one stabilizer in improving the muscle performance of a subject, such as an athlete. According to some embodiments, the athlete is a professional athlete.

The term "administering" or "administration of" a substance, a compound or a composition to a subject can be carried out using one of a variety of methods known to those skilled in the art. For example, a compound or a composition can be administered enterally or parenterally. Enterally refers to administration via the gastrointestinal tract including per os, sublingually or rectally. Parenteral administration includes administration intravenously, intradermally, intramuscularly, intraperitoneally, subcutaneously, ocularly, sublingually, intranasally, by inhalation, intraspinally, intracerebrally, and transdermally (by absorption, e.g., through a skin duct). A compound or a composition can also appropriately be introduced by rechargeable or biodegradable polymeric devices or other "drug-release" and "controlled-release" devices, e.g., patches and pumps, or formulations, which provide for the extended, slow or controlled release of the compound or composition. Administering can also be performed, for example, once, a plurality of times, and/or over one or more extended periods. In some aspects, the administration includes both direct administration, including self-administration, and indirect administration, including the act of prescribing a drug or medical food.

According to some embodiments, the administration is an oral administration. According to other embodiments, the administration is a sublingual administration. According to further embodiments, the administration is a combined oral and sublingual administration.

According to certain embodiments, administration, e.g. oral, sublingual, or combined, comprises administering less than 200 mg/kg per day of calcium as stabilized ACC. The dose according to any one of the aspects and embodiments of the present invention refers to the amount of elemental calcium in the ACC. According to one embodiment, the method of the present invention comprises administering less than 150 mg/kg/day or less than 100 mg/kg/day of calcium as stabilized ACC. According to another embodiment, the administered dose of ACC is less than 50 mg/kg/day, less than 30 mg/kg/day, or less than 20 mg/kg/day of calcium as stabilized ACC. According to some embodiments, administration according to the present invention, e.g. oral, sublingual or combined administration comprising administration of 5 to 150, 10 to 120, 15 to 100, 20 to 80, 30 to 70 or 40 to 60 mg/kg/day of calcium as stabilized ACC. According to certain embodiments, administration according to the present invention, e.g. oral, sublingual or combined administration comprising administration of 5 to 80, 10 to 75, 15 to 70, 20 to 65, 25 to 60, 30 to 55, 35 to 50 or 40 to 45 mg/kg/day of calcium as stabilized ACC. According to some embodiment, administration according to the present invention, e.g. oral, sublingual or combined administration comprising administration of about 10 to about 45, about 15 to about 40, about 20 to about 35 mg/kg/day of calcium as stabilized ACC. According to further embodiment, administration according to the present invention, e.g. oral, sublingual or combined administration comprising administration of 0.1 to 30, 0.2 to 28, 0.3 to 26, 0.5 to 24, 1 to 22, 2 to 20, 3 to 18, 3 to 16, 4 to 15, 5 to 14, 6 to 12, or 8 to 10 mg/kg/day of calcium as stabilized ACC. According to some embodiments, administration according to the present invention, e.g. oral, sublingual or combined administration comprising administration of 0.2 to 10, 0.5 to 8, 0.8 to 6, 1 to 5, 1.5 to 4, or 2 to 3 mg/kg/day of calcium as stabilized ACC. According to another embodiment, the administration comprises administration of 500 to 8000 mg/day, 800 to 6000, or 100 to 4000 mg/day of ACC. According to some embodiments, the administration comprises administration of from 200 to 3000 mg/day, from 400 to 2500 or from 600 to 2000 mg/day of calcium as stabilized ACC. According to other embodiments, the administration comprises administration of from 800 to 4000 mg/day, from 1000 to 3000 or from 1500 to 2500 mg/day of calcium as stabilized ACC.

According to some embodiments, the administration e.g. oral, sublingual or combined administration, comprises daily administering of about 600 to about 23,500 mg of ACC. According to one embodiment, the administration comprises administering of 600 to 20,000, 800 to 18,000, 1,000 to 15,000, 1,200 to 12,000, 1,500 to 10,000, and 2000 to 8000 mg/day of ACC. According to some embodiments, the administration comprises administering of 1000 to 12000, 2000 to 11000, 3000 to 10000, 3500 to 9000, 4000 to 8000 mg/day of ACC.

According to some embodiments, the administration comprises administering of 10 to 350 mg/kg/day of stabilized ACC. According to some embodiment, the administration comprises administering of 20 to 300, 30 to 250 40 to 200, 50 to 150 or 30 to 120 mg/kg/day of ACC.

According to some embodiments, the administration comprises administration in a single dose or in multiple separated doses. For Example, the daily dose may be separated and administered in 2, 3, 4, 5, 6, 7, 8, 9, 10, 11 or 12 separate doses.

According to some embodiments, the administration is short-term administration, e.g. administration for at least 1, 2, 3, 5, or 7 days. According to other embodiments, the administration is for 1, 2, 3, or 4 weeks. According to further embodiments, the administration is for a long term such as for 1, 2, 3, 4, 5, 6, 7, 8, 9, 10, 11, or 12 months. According to other embodiments, the administration for one or more years such as 2, 3, 4, 5, or more years.

According to some embodiments, the composition for sublingual administration is in the form of a powder of ACC. The powder for sublingual administration is formed of ACC particles.

The term "particles" as used herein refers to a discrete microparticle or a nanoparticle of ACC stabilized by the stabilizer as defined hereinabove, as well as to the aggregates or agglomerates thereof. According to some embodiments, the particles are primary particles of the stabilized ACC. The basic nanoparticles are in the range of 5 to 500 nm or 10 to 300 nm or 20 to 100 nm. In many cases, these nanoparticles immediately agglomerate and aggregate into much larger secondary particles. These aggregation and agglomeration can be then broken by milling and dissolution techniques into smaller particles. According to other embodiments, the particles are agglomerates or aggregates of the primary particles, i.e. secondary particles. The term "particle size" as used herein refers to a measurement of a representative diameter of the secondary particles such as an aggregate or a broken aggregate in at least one dimension.

The particle size of agglomerates can be tailored into ranges by a combination of milling and sieving techniques. In some embodiments, at least 70% of the processed particles of the composition have a particle size of 600 μm or less. In other embodiments, at least 80%, at least 85%, at least 90% or at least 95% of the particles of the composition have a particle size of 600 μm or less. In some embodiments, at least 80%, at least 85%, at least 90% or at least 95% of the particles of the composition have a particle size of 500 μm or less. In some embodiments, at least 80%, at least 85%, at least 90% or at least 95% of the particles of the composition have a particle size of 400 μm or less. In some embodiments, at least 80%, at least 85%, at least 90% or at least 95% of the particles of the composition have a particle size of 300 μm or less. In some embodiments, at least 80%, at least 85%, at least 90% or at least 95% of the particles of the composition have a particle size of 200 μm or less. In some embodiments, at least 80%, at least 85%, at least 90% or at least 95% of the particles of the composition have a particle size of 100 μm or less. In some embodiments, at least 80%, at least 85%, at least 90% or at least 95% of the particles of the composition have a particle size of 70, 50, 30 μm or less. According to some embodiments, the particle size is from about 20 to about 500 μm, from about 30 to about 450 μm or from about 50 to about 400 μm.

According to any one of the above embodiments, the ACC is a stabilized ACC, i.e. ACC that maintains amorphous for a long period even in humid conditions or in an aqueous environment According to any one of the above embodiments, the ACC is stabilized by at least one stabilizer. The terms "stabilizing agent" and "stabilizer" are used herein interchangeably and refer to any molecule, ion or substance that contributes to preserving calcium carbonate in the amorphous state during ACC production, formulating and/or storage. According to the teachings of the present invention, the ACC acts as an active agent conferring improvement in athletic and muscle performance. Any ACC that remains stable may be used according to the teaching of the present invention. Any compound that may stabilize ACC in its amorphous form is suitable for the implementation of the present invention. The terms "stable ACC" and "stabilized ACC" are used herein interchangeably and indicates that calcium carbonate is maintained in its amorphous form for a prolonged period of time having less than or about 30% of conversion to a crystalline form.

The essence of the present invention is in providing ACC to athletes and therefore improving their performances. As long as ACC remains amorphous, this goal is achieved. Many stabilizers were previously shown, e.g. by the Applicant, to effectively stabilize ACC in the amorphous form in aqueous condition. Some of the stabilizers are listed below.

In certain embodiments, the stabilizing agent is a single agent. In other embodiments, the use of several stabilizing agents is encompassed. In some cases, the stabilizers are present within the molecular matrix of the ACC particles. In some cases, they are deposited externally and in other cases, they are both internal or external. The internal stabilizers or combination of stabilizers can be the same or different than the external ones.

ACC Stabilizers

The stabilizer may comprise a molecule having one or more functional groups selected from, but not limited to, hydroxyl, carboxyl, ester, amine, phosphino, phosphono, phosphate, sulfonyl, sulfate or sulfino groups. The hydroxy bearing compounds, combined with the hydroxide, optionally also bear other functions like carboxyl, etc. but with the hydroxyl not being esterified.

According to some embodiments, the stabilizer has low toxicity or no toxicity to mammalian cells or organism, and in particular to a human being. According to some embodiment, the stabilizer is of food, nutraceutical or pharmaceutical grade.

In certain embodiments, the ACC stabilizing agent is independently at each occurrence, an organic acid, phosphorylated, phosphonated, sulfated or sulfonated organic compound, phosphoric or sulfuric ester of a hydroxyl carboxylic acid, an organoamine compound, an organic compound comprising a hydroxyl, an organophosphorous compound or a salt thereof, phosphorylated amino acids and derivatives thereof, a bisphosphonate compound, an organophosphate compound, an organophosphonate compound, an inorganic phosphorous acid, an organic compound having multiple functional groups as defined above, an inorganic phosphate and polyphosphate compound, an organic compound having a polyphosphate chain, an organic surfactant, a bio-essential inorganic ion, or any combination thereof.

According to some embodiments, the stabilizer is an organic acid. According to certain embodiments, the organic acid is selected from ascorbic acid, citric acid, lactic acid, acetic acid, oxalic acid, malonic acid, glutaconic acid, succinic acid, maleic acid, lactic acid, aconitic acid, and optionally include compounds having at least two carboxylic groups and molecular weight not larger than 250 g/mol, such as citric acid, tartaric acid, malic acid, etc. According to one particular embodiment, the stabilizer is citric acid.

In another embodiment, the phosphoric ester of hydroxyl carboxylic acids is a phosphoenolpyruvate. In another embodiment, the phosphoric or sulfuric esters of hydroxyl carboxylic acids comprise amino acids. Examples of such esters are phosphoserine, phosphothreonine, sulfoserine, sulfothreonine and phosphocreatine.

The hydroxyl bearing compounds combined with hydroxide may comprise, for example, mono-, di- tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment, of the present invention.

Some specific unlimited examples for such ACC stabilizers that include phytic acid, citric acid, sodium pyrophosphate dibasic, adenosine 5'-monophosphate (AMP) sodium salt, adenosine 5'-diphosphate (ADP) sodium salt and adenosine 5'-triphosphate (ATP) disodium salt hydrate, phosphoserine, phosphorylated amino acids, food grade surfactants, sodium stearoyl lactylate, and combinations thereof.

According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and hydroxyl bearing organic compounds, selected from mono-, di-, tri-, oligo- and polysaccharides, for example, sucrose, mannose, glucose.

The hydroxyl bearing compound may further comprise at least one alkali hydroxide, such as sodium hydroxide, potassium hydroxide and the like. The phosphorylated acids may be present in oligopeptides and polypeptides. In other embodiments, of the invention, the stabilizer is an organic acid selected from monocarboxylic acid or multiple carboxylic acid, e.g. dicarboxylic acid or tricarboxylic acid. Each possibility represents a separate embodiment, of the invention. The organic acid may be as defined above.

In some embodiments, of the invention, the ACC stabilizer is selected from phosphorylated amino acids, polyols and combinations thereof. In some embodiments, the stable ACC comprises a phosphorylated compound as a stabilizer wherein the phosphorylation is performed on the hydroxyl group of an organic compound. In some embodiments, the stable ACC comprises a stabilizer selected from the group consisting of citric acid, phosphoserine, phosphothreonine and combinations thereof. The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, $\alpha$-D-galactosamine 1-phosphate, 2-phospho-L-ascorbic acid trisodium salt, $\alpha$-D-galactose 1-phosphate dipotassium salt pentahydrate, $\alpha$-D-galactosamine 1-phosphate, O-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof.

In some embodiments, the stabilizers can be bio-essential inorganic ions including, inter alia, Na, K, Mg, Zn, Fe, P, S, N, P, or S in the phase of oxides, or N as ammonia or nitro groups.

The stabilized ACC may be stabilized by more than one stabilizer, e.g. 2, 3, or more stabilizers. The stabilizers can be added during the synthesis and precipitation of the ACC primary particles and they are defined as "internal stabilizer". Stabilizers can be added after the synthesis and bind to the external surface of the particles. They are defined as "external stabilizers". In some embodiments, where both internal and external stabilizers are used the internal stabilizer and the external stabilizer are similar. In other embodiments, the internal stabilizer and the external stabilizer are different stabilizers. The internal and the external stabilizers may be each independently as defined hereinabove and each can be a combination of more than one type of stabilizer.

The stable ACC can comprise more than two stabilizers, wherein one or more stabilizers are added to the ACC during the formation and precipitation of the ACC.

According to some embodiments, the at least one stabilizer is selected from the group consisting of a polyphosphate, bisphosphonate, phosphorylated amino acid, citric acid, and any combination thereof. In some embodiments, more than one stabilizer, e.g. 2, 3, or 4 stabilizers are added.

According to one embodiment, ACC is stabilized by a combination of phosphoserine and citric acid. According to another embodiment, ACC is stabilized by a combination of triphosphate and citric acid.

According to some embodiments, the stabilizer is a polyphosphate or pharmaceutically acceptable salts thereof. According to some embodiments, the polyphosphate is a physiologically compatible, water-soluble polyphosphate salt selected from the group consisting of sodium, potassium, and any other essential cation of polyphosphate. In one embodiment, the polyphosphate is organic or inorganic polyphosphate. The term "polyphosphate" as used herein refers to polymeric esters of PO4. According to some embodiments, the polyphosphate is a physiologically compatible water-soluble polyphosphate salt selected from the group consisting of sodium and potassium polyphosphate. In some embodiments, the polyphosphate is an inorganic polyphosphate or pharmaceutically acceptable salts thereof. Not-limiting examples of such salt are Na, K, Mg, Mn, and Zn. According to some embodiments, the inorganic phosphate comprises 2 to 10 phosphate groups, e.g. 2, 3, 4, 5, 6, 7, 8, 9, or 10 phosphate groups. According to some embodiments, the inorganic polyphosphate is selected from pyrophosphate, triphosphate, and hexametaphosphate. According to one embodiment, the stabilizer is pyrophosphate or pharmaceutically acceptable salts thereof such as sodium pyrophosphate. According to another embodiment, the stabilizer is triphosphate or pharmaceutically acceptable salts thereof such as sodium triphosphate. The term "triphosphate" and "tripolyphosphate" are used herein interchangeably. According to a further embodiment, the stabilizer is hexametaphosphate or a pharmaceutically acceptable salt thereof such as sodium hexametaphosphate.

According to some embodiments, the stabilizer is a bisphosphonate or pharmaceutically acceptable salts thereof. The non-limiting examples of salt are Na, K, Mg, Mn and Zn.

The term "bisphosphonate" as used herein refers to organic compounds having two phosphonate (PO(OH)$_2$) groups. The term further relates to compounds having a backbone of PO$_3$-organic-PO$_3$. Most typical is a series of bisphosphonates that are used as pharmaceuticals for treating osteoporosis. According to some embodiments, the bisphosphonate is selected from the group consisting of etidronic acid, zoledronic acid, medronic acid, alendronic acid, and a pharmaceutically acceptable salt thereof. According to some embodiments, the stabilizer is an etidronic acid or a pharmaceutically acceptable salt thereof. According to another embodiment, the stabilizer is a zoledronic acid or a pharmaceutically acceptable salt thereof. According to a further embodiment, the stabilizer is a medronic acid or a pharmaceutically acceptable salt thereof. According to certain embodiments, the stabilizer is alendronic acid or a pharmaceutically acceptable salt thereof.

According to certain embodiments, the stabilizer is a phosphorylated amino acid. According to one embodiment, the phosphorylated amino acid is phosphoserine. According to another embodiment, the phosphorylated amino acid is phosphothreonine.

According to some embodiments, the ACC composition comprises a combination of the stabilizers disclosed above.

According to some embodiments, the stabilizer is an inorganic polyphosphate or a bisphosphonate as defined hereinabove, and the molar ratio between P atoms of the stabilizer and Ca atoms of the ACC (P:Ca molar ratio) is about 1:90 to 1:1. In one embodiment, the P:Ca molar ratio is about 1:40 to about 1:1. In a further embodiment, the P:Ca molar ratio is about 1:35 to about 1:2. In certain embodiments, the P:Ca molar ratio is about 1:30 to about 1:3. In certain embodiments, the P:Ca molar ratio is about 1:28 to about 1:3. In other embodiments, the P:Ca molar ratio is about 1:25 to about 1:4. In further embodiment, the P:Ca molar ratio is about 1:20 to about 1:5. In another embodiment, the P:Ca molar ratio is about 1:20 to about 1:6. In a particular embodiment, the P:Ca molar ratio is about 1:15 to about 1:5. In another particular embodiment, the P:Ca molar ratio is about 1:25 to about 1:5. According to some embodiments, such inorganic polyphosphate is pyrophosphate, triphosphate, hexametaphosphate or a pharmaceutically acceptable salt thereof. According to another embodiment, the bisphosphonate is alendronic acid, etidronic acid, zoledronic acid or medronic acid and the P:Ca molar ratio is as defined hereinabove.

According to some embodiments, the calcium content (Ca content) of such compositions comprising stabilizers is about 1 wt % to about 39 wt %, about 5 wt % to about 39 wt %, about 10% to about 39 wt %, about 15% to about 39 wt %, about 20 wt % to about 38 wt %, about 25 wt % to about 38 wt %, or about 30 wt % to about 38 wt % of the dry ACC particles The terms "Ca content" and "calcium content" is used herein interchangeably and refer to the content of calcium of the ACC in the final composition.

In certain embodiments, the P:Ca molar ratio is about 1:40 to about 1:1, and the Ca content is about 20 wt % to about 39 wt %. In some embodiments, the molar ratio is 1:28 to about 1:3, and the Ca content is about 30 wt % to about 38 wt % of the dry ACC particles. In another embodiment, the molar ratio is 1:25 to about 1:5, and the Ca content is about 30 wt % to about 36 wt % of the dry ACC particles.

According to some embodiments, the stabilized ACC powder comprises absorbed and adsorbed water, from about 1 wt % to about 18 wt %, from about 4 wt % to about 15 wt %, and from about 6 wt % to about 10 wt %. According to some embodiments, the stabilizer is polyphosphate or bisphosphonate and the molar ratio between P atoms of the stabilizer and Ca atoms of the ACC is about 1:90 to 1:1.

According to some embodiments, the stabilizer is selected from the group consisting of a polyphosphate, phosphorylated amino acid, bisphosphonate, citric acid, tartaric acid and any combination thereof. According to one embodiments, the polyphosphate is selected from the group consisting of triphosphate, pyrophosphate, and hexametaphosphate, the phosphorylated amino acid is phosphoserine or phosphothreonine, and the bisphosphonate is selected from the group consisting of alendronate, etidronic acid, zoledronic acid and medronic acid. According to some embodiments, the polyphosphate is an inorganic polyphosphate.

According to one embodiment, the stabilizer is selected from selected from the group consisting of organic acids, phosphorylated, phosphonated, sulfated or sulfonated organic compound, phosphoric or sulfuric esters of hydroxy carboxylic acids, phosphorylated amino acids, bisphosphonate, organic polyphosphate, hydroxyl bearing organic compounds, derivatives thereof, proteins and any combinations thereof.

According to another embodiment, the stabilizer is selected from the group consisting of phosphoserine, adenosine triphosphate, adenosine diphosphate, phytic acid, citric acid, etidronic acid, pyrophosphate, polyphosphate, inorganic triphosphate, hexamethaphosphate, ethanol, and any combination thereof.

In most cases, the ACC contains 1 to 20 wt % and preferably no more than 10 wt % of adsorbed water and maintain its stabilization in the presence of a stabilizer and further storage in dry conditions. ACC powder that was used in the examples contained about 6 to 10 wt % of water when formulated. In terms of calcium content, it means that the calcium content in ACC is in a practical range of 28 to 38 wt % of its composition. For practical calculation, the average calcium content is defined as 30 wt % in this application.

The term "pharmaceutical composition" as used herein refers to any composition comprising at least stabilized ACC, and optionally at least one additional pharmaceutically acceptable carriers, stabilizers, and/or bulking agents.

According to any above aspects and embodiments, the composition of the present invention is a food supplement. Thus is some embodiments, the present invention provides a food supplement comprising amorphous calcium carbonate (ACC) stabilized by at least one stabilizer for use in improving the athletic performance of a subject.

According to some embodiments, the use is a non-therapeutic use. In some embodiments, the present invention provides a non-therapeutic use of a food supplement comprising amorphous calcium carbonate (ACC) stabilized by at least one stabilizer in improving the athletic performance of a subject. According to some embodiments, improving athletic performance comprises improving muscle performance.

Formulations of the composition of the present invention may be adjusted according to the required applications. In particular, the composition may be formulated using a method known in the art to provide a rapid, continuous or delayed release of the active ingredient after administration to mammals. For example, the formulation may be any one selected from plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules. According to some embodiments, the composition is a powder. According to certain embodiments, the composition is a powder for a sublingual administration. According to other embodiments, the composition is in the form of a tablet or capsules for oral administration. According to some embodiments, the composition for oral administration may be an enteric-coated composition or an enteric capsule.

Formulations can also include excipients for aiding the manufacturing, storage, and efficiency of the administration. Examples are silicon dioxide and microcellulose as anticaking agents, magnesium stearate as a lubricant, and sucralose, mannitol, sorbitol, erythritol, menthol and citric acid as flavoring agents.

According to some embodiments, the composition is a nutraceutical composition. As used herein, the term "nutraceutical composition" refers to a composition suitable for use in human beings or animals, comprising one or more natural products with therapeutic action which provide a health benefit or have been associated with disease prevention or reduction.

The term "food supplement" is used to mean a product containing said composition and intended to supplement the food by providing nutrients that are beneficial to health according to any acceptable directive, such as European directive. For example, a food supplement may be a capsule or a tablet for swallowing, or powder or small vial to mix with food and providing beneficial health effects. The food supplement may be also formulated as a sublingual composition. The food supplement may comprise aside the active agent edible carrier and/or excipients. According to some embodiments, the edible carrier and/or excipient is a pharmaceutically acceptable carrier and/or excipient.

The term "edible carrier" refers to compounds, materials, compositions, and/or dosage forms that are suitable for use in contact with the tissues of a subject. Each carrier must also be "acceptable" in the sense of being compatible with the other ingredients of the formulation. The term "edible carrier" as used herein means a material that can be administered, consumed, digested or passed through the digestive system of an animal or human without any toxic effect. These edible carrier materials can exist as either a solid or liquid at room temperature.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, and the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate.

According to any one of the above embodiments, the composition of the present invention, is formulated in any known form such as powder, suspension, tablet, or capsule.

Having now generally described the invention, the same will be more readily understood through reference to the following examples, which are provided by way of illustration and are not intended to be limiting of the present invention.

EXAMPLES

Example 1—Preparation of Sublingual Composition Comprising Stabilized ACC

ACC stabilized by sodium triphosphate and citric acid solid composition was prepared as described in WO2016193982 A1 with water content of from 8-10% as measured by loss when drying. For preparing the powder for sublingual administration, the obtained solid was further milled to the size of below 0.4 millimeter. The powder was mixed with excipients such as: anticaking agent, such as silicon dioxide, lubricant such as magnesium stearate and sweetening and flavoring compounds such as sucralose, mannitol, sorbitol, erythritol, mint and citric acid and used by sublingual administration. The ACC tablet formulation for oral administration was prepared as described in WO 2016/193982, and corresponds with the commercial product Density®, developed and marketed by the applicant.

Example 2. Influence of ACC on Athletes' Performances and Recovery

Aim:

This pilot study aimed at comparing the ability of athletes taking sublingually amorphous calcium carbonate (ACC) and crystalline calcium carbonate (CCC) to perform intense physical activity using the Wingate anaerobic test and lactate measurements before and after the test. The sublingual administration of ACC powder formulation allows to bypass stomach.

Study Procedure

The study was done with two professional cyclists, as a double-blind crossover test, using ACC or CCC (control) as test items. The subjects received the first test item for 3 days, and performed Wingate test. After a cleaning period of 3 days the routine was repeated with the second test item. The efficacy of CCC and ACC on performing Wingate test was evaluated for each cyclist.

Each subject received ACC or CCC formulations in sachets that looked identical from the outside, with the exception of the writing B (for CCC) or D (for ACC). Each sachet contained 250 mg elemental calcium in the form of powder (about 740 mg of ACC). The test item was administered by the sublingual route for 5 minutes. The total daily dose was 2,250 mg elemental calcium as ACC (corresponding to about 6660 mg of ACC). On the day of the Wingate test, the subjects received 2 sachets before the test and 1 sachet afterward. Then, for the next 3 days, they received no treatment (see Table 1).

The ACC powder and tablets that were used in the experiments were primarily prepared for the purpose of calcium supplementation. Hence, their dosage was documented by their exact calcium content. However, the commercial ACC (manufactured by Amorphical) may contain various amounts of strongly adsorbed water, which does not affect its long-term stability. Hence, for calculation purposes based on an average measurements of commercial batches, the ACC amount is calculated in the examples on the approximate basis of 30-35% calcium content of ACC.

TABLE 1

Experimental procedure

| Day | Friday-Sunday | Monday (Wingate test) | Tuesday-Thursday | Friday-Sunday | Monday (Wingate test) |
|---|---|---|---|---|---|
| Treatment | ACC/CCC | ACC/CCC | No Treatment | CCC/ACC | CCC/ACC |
| Dose/day | 9 sachets | 3 sachets | 0 | 9 sachets | 3 sachets |

Wingate anaerobic test is an anaerobic exercise test, performed on a stationary bicycle that measures peak anaerobic power and anaerobic capacity. The test was performed as follows: after a warmed up the subject cycled for 30 seconds in full power followed by 2 minutes of a rest interval, after which the cycled again for 30 seconds in full power, followed by 2 minutes of rest, and then a third round of cycling for 30 seconds in full power. FIG. 1 describes the test design performed by each of the subjects.

Lactate levels were measured using EKF Lactate Scout device prior to performing the Wingate test and tested again 3, 5, 7, 9 and 15 minutes after the test.

The peak power (PP) for each cyclist, as measured during each of the 3 repeats of the Wingate test are presented in FIG. 2. The Power is measured according to the following equation:

$$\text{Power} = \text{Force}(kg) \times \text{Distance}(m) \div \text{Time}(s)$$

wherein the force is calculated as 7.5% of the athlete mass and the distance is the number of revolutions multiplied by the distance per revolution (in meters).

FIG. 3 shows the Fatigue Index (FI), calculated for each cyclist. This index corresponds to anaerobic capacity or endurance.

Figure 2A:
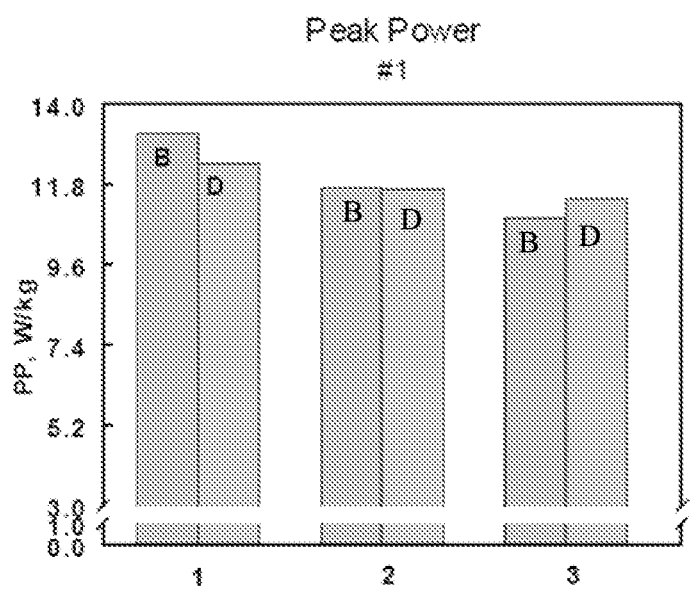
FIG. 2 shows power peak and mean power exerted by two cyclists; Cyclist 1: power peak (FIG. 2A) and mean power (FIG. 2B); Cyclist 1: power peak (FIG. 2C) and mean power (FIG. 2D). B stands for administration of CCC, D for administration of ACC. Plac stands for administration of CCC as a placebo control.
Figure 2B:
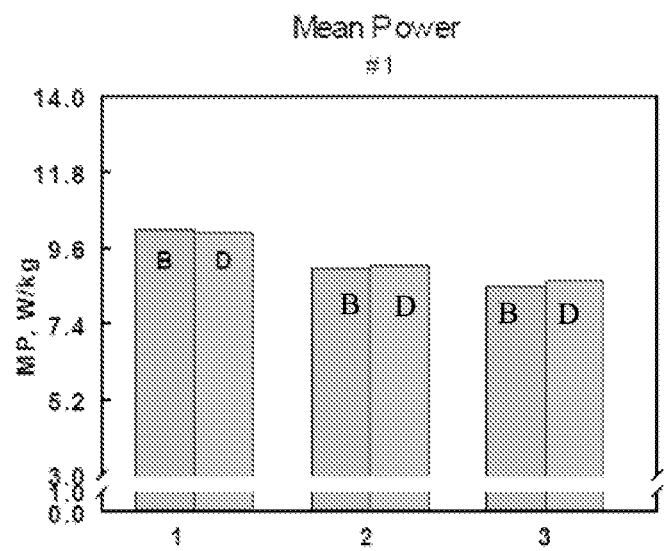
Figure 2C:
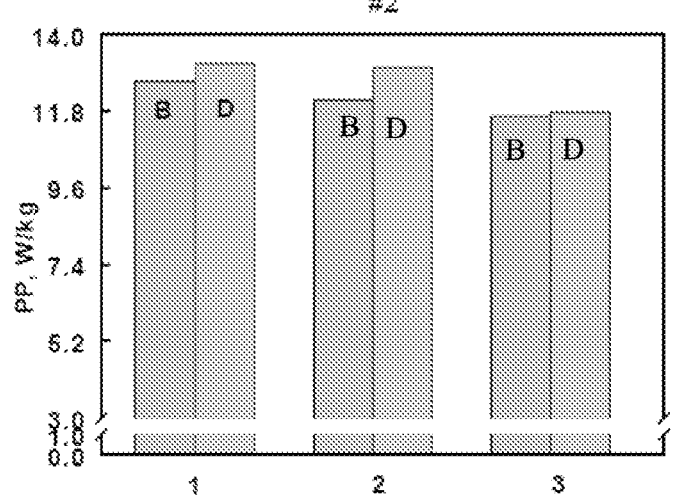
Figure 2D:
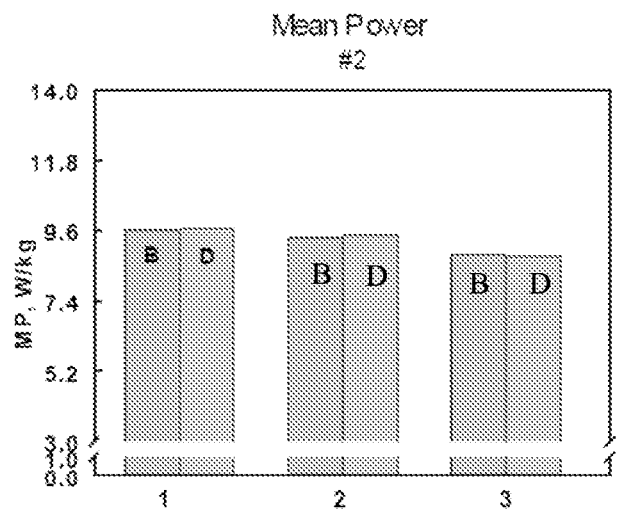

The results presented in FIG. 2C demonstrate that subject #2 had an improved performance when taking ACC on maximal strength, which was maintained for the next 2 performances compared to the case of CCC administration. FIG. 2A shows that initial performance of Subject #1 was better with CCC than with ACC administration. However, he was able to preserve higher performance using ACC in subsequent cycles, much better than with CCC. This observation was reinforced by the Fatigue Index illustrated in FIG. 3.

The Fatigue Index measures the rate at which power declines from peak power to the lowest power (5 last secs) of the same 30 sec test. A higher fatigue index represents lower ability to maintain power, i.e., lower endurance. It is calculated according to the following equation:

$$FI = \left[ \frac{(\text{Highest 5s anaerobic power} - \text{Lowest 5s anaerobic power})}{\text{Highest 5s anaerobic power}} \right] \times 100$$

Figure 3A:
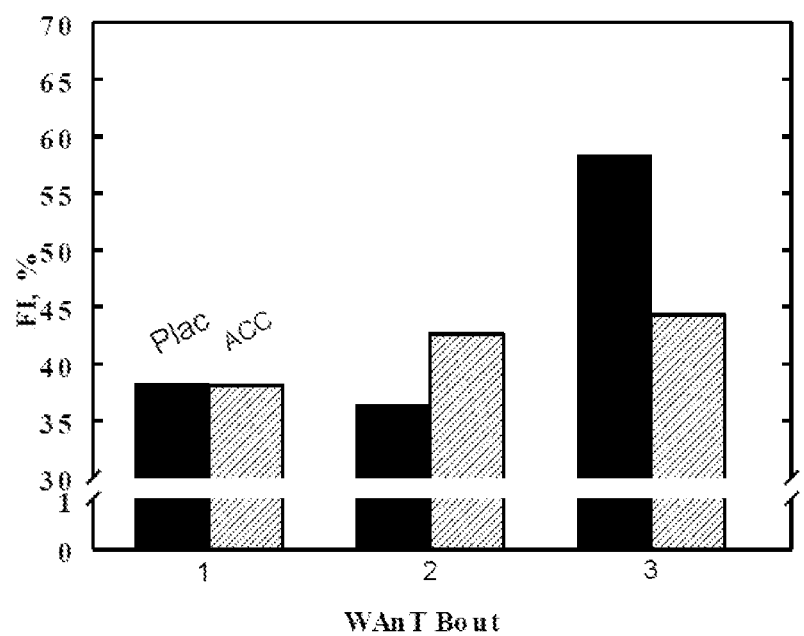
FIG. 3 shows calculated fatigue indices for Cyclist 1 (FIG. 3A) and Cyclist 2 (FIG. 3B).

As shown in FIG. 3A, Cyclist #1 had the same fatigue index in the first session for ACC and CCC and comparable fatigue indices after the second cycling session. However, in the third cycling session, the index was much lower after using ACC than with CCC. As for Cyclist #2, ACC has shown a decrease in the fatigue index in both the second and third cycling session after taking ACC in comparison to taking CCC.

Figures 3B, 4A:
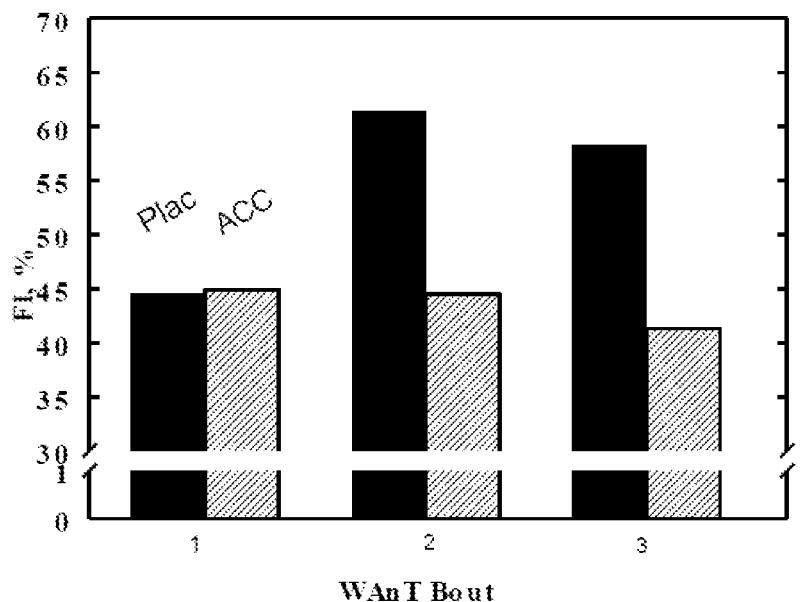
FIG. 4 shows lactate levels in the blood of cyclist 1 (FIG. 4A) and cyclist 2 (FIG. 4B). B (triangles) stands for administration of CCC, D (circles) for administration of ACC.
Figure 4B:
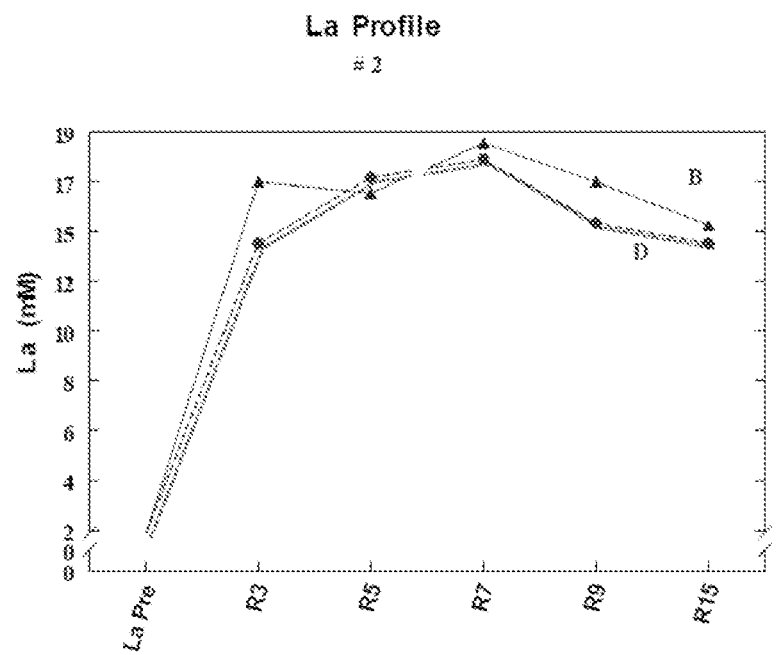

Lactate measurements (FIG. 4) show that Cyclist #1 had an improved capability to remove lactate from the blood after taking ACC than after taking CCC (seen by lower lactate levels in FIG. 4A). A similar trend was seen for Cyclist #2 (FIG. 4A=B). This evidence corresponds to better performance due to faster recovery rates.

These results clearly indicate that ACC has a positive effect on the ability of cyclists to maintain high performance as seen by the PP values, which barely declined for both athletes after taking ACC compared to after taking CCC. Examining the fatigue index results reveals that it was much lower after taking ACC than after taking CCC for both cyclists, especially during the last cycling session which is the most tiring session.

Example 3. Case Studies with Highly Trained and/or Top Performing Athletes

Several case studies of athletes are described. The athletes started receiving ACC sublingually due to different physiological conditions such as non-healing fractures, inflammations and persistent pains. Following rapid recovery from the pathological condition(s) (if any present), the athletes kept taking ACC and most began improving their achievements and break their own records. Athletes consumed between 2 and 10 sachets per day, containing ACC powder for sublingual administration, each sachet containing 200 or 250 mg of calcium (corresponding to about 620 and 740 mg of ACC, respectively). The powder for sublingual administration comprised 80-90 wt % of stabilized ACC, anticaking agent, such as silicon dioxide, lubricant such as magnesium stearate and sweetening and flavoring compounds such as sucralose, mannitol, sorbitol, erythritol and citric acid. In some cases, the athletes received oral formulations (tablets), each comprising 200 mg elemental calcium in the form of ACC, in addition to the sublingual doses.

Athlete 1 (Swimmer, Male)

Athlete 1 is a swimmer with international success for over 8 years. He suffered from painful osteolysis of clavicle and was treated with steroid injections for over a year. After 21 days of administering 2400 mg/day of calcium in ACC sublingually (~7440 mg of ACC), the pain was gone. The athlete continued taking 2000 mg/day of calcium as ACC (~7000 mg of ACC), and after 60 days from beginning of administration, he set a new national record in 200 m individual medley and in 100 m individual medley. In an international championship. In the 100 m swim he broke his own record by more than half a second After 80 days he achieved additional new personal records including an improvement of his best record in 200 m breaststroke by 1.2 sec.

Athlete 2 (Runner, Male)

Athlete 2, a long-distance runner with national championship records, was diagnosed as suffering from stress fracture of sacrum. After 9 days of treatment with ACC, by administering 1800 mg/day of calcium as ACC (~5580 mg of ACC) administered sublingually, the pain disappeared. The athlete continued the ACC administration as follows: 200 (~620) mg calcium as ACC oral tablet twice a day with the addition of 1,500 mg calcium as ACC (~4440 mg) of the sublingual ACC dose for about 20 additional days, after which he returned to regular training. The athlete indicated that each day he could handle more extensive training without feeling fatigue. The Athlete continued with ~5680 mg/day of ACC, administered sublingually and orally. After 52 days he broke his personal record in marathon running by reducing more than 4 minutes and did it again after 84 days and 136 days, while participating in international competitions (another time reduction by more than 3 minutes).

Athlete 3 (Crossfit, Female)

Athlete 3, a crossfit athlete with national records, suffered from overly trained knee resulted in swelling. She was previously treated with Etopan (etodolac). Upon ceasing the etodolac treatment she began ACC treatment by sublingual administration of 1500 mg/day of calcium as ACC (~4440 mg/day of ACC). The swelling and pain were completely gone after two days of treatment. The Athlete continued taking sublingually the same dose of ACC. Within a period of 30-90 days she broke more than 10 personal records as follows (% improvements in parentheses): Snatch from blocks (11.4%), Back Squat (7.8%), Front Squat (5.0%), Jerk 101 Kg (1.0%), P.R. Clean 2 Front Squat (5.9), Clean+ Front Squat (11.8%), Hang Power Clean (6.3%), Power Snatch (2.9%), Snatch+Overhead Squat (6.7%), Snatch (0.6%), Press for 2 reps (10.0%).

Athlete 4 (Runner, Male)

Athlete 4, a long-distance runner with national records, suffered from hip stress fracture and inflammation of adductor magnus and longus. The Athlete was treated with of 1,500 mg/day of calcium as ACC sublingually (~4440 mg/day of ACC) for 14 days and increased the dose to 1,750 mg/day afterwards (~5180 mg/day of ACC). The pain was gradually subdued: 80% of the pain disappeared after 14 day, and completely disappeared after 19 days. The Athlete continued taking sublingually the same dose of ACC. After 54 days he broke 2 records in 20,000 meters running and after another 27 days his record in marathon running improved by more than 2 minutes.

Athlete 5 (Runner, Male)

Athlete 5 was diagnosed as suffering from hamstring tendonitis. The athlete was treated with 1,400/day of calcium as ACC (~4340 mg/day), sublingually. The Athlete reported gradual calming of pains: After 14 days 50% of the pain disappeared and after 45 days of additional sublingual administration, he reported that 95% of the pain disappeared. The Athlete continued taking the same dose of ACC sublingually. After 56 and 83 days from the beginning of the treatment, the Athlete broke his personal record in 3000 m running by 7 and 6.5 second, respectively.

Athlete 6 (Swimmer, Female)

Athlete 6 reported performance regression for almost 4 years without any injury, most likely due to age-related decline. After 30 days of administering ~5180 mg/day of ACC sublingually (1750 mg of calcium), the Athlete reported that she felt stronger. After additional 30 days, she broke her personal record at 200 freestyle.

Athlete 7 (Runner, Male)

Athlete 7 suffered from level-3 stress fracture of a tibia. After 14 days of sublingual administration of 2200 mg/day calcium (~6820 mg/day of ACC), using a combination of sublingual and oral doses, the athlete reported pain disappearance and returned to regular training. The athlete continued taking ~5680 mg ACC. The athlete reported great feeling during training and performance improvement. After 59 days he broke his personal record in half marathon by more than 9 minutes. After additional 12 days he broke his recent personal record in half marathon by another 3 minutes.

Athlete 8 (Runner, Female)

Athlete 8 suffered from inflammation as a result of a bulging disc, accompanied with a decreased range of muscle motion (muscle stiffness). After 14 days of sublingual administration of 1500 mg/day of calcium as ACC (~4440 mg/day of ACC) the pain decreased during running. After 30 days the pain dropped from level 10 to 3. The motion range was improved and the athlete reported rapid recovery right after running. She became much more flexible, with higher endurance. Her performance has improved immeasurably. Her recovery from training to training is fantastic. Her heart rate during intense exercise dropped significantly. This recovery changed all her abilities. This has reversed her body's age (at the age of 49) she felt 10 to 15 years younger.

Example 4—the Effect of Different Sources of Calcium Carbonate on the pH of Media Two commercial media, Dulbecco's phosphate-buffered saline (DPBS) and Gibco Dulbecco's Modified Eagle Medium: Nutrient Mixture F-12 (DMEM/F12), with 10% Fetal Bovine Serum (FBS) were used to evaluate the pH effect of different sources of calcium carbonate. DPBS is Dulbecco's Phosphate Buffered Saline, generally serves as an isotonic saline solution or buffer for washing cells and tissues and intends to provide a buffer system for maintaining cell culture media in the physiological range of 7.2-7.6.

DMEM/F12 is a widely used basal medium for supporting the growth of many different mammalian cells. DMEM/F12 medium+10% FBS was used to maximally mimic the environment of the body fluids.

Three sources of calcium carbonate were used ACC, Sodium bicarbonate (SBC) and Crystalline Calcium Carbonate (CCC).

ACC suspension was prepared by adding 36 ml calcium chloride di-hydrate solution 3.10% w/v mixed with 4 ml water and 10 ml triphosphate solution 0.56% w/v with 40 ml sodium carbonate solution 1.95% to precipitate ACC, followed by addition of 10 ml of stabilizing solution containing triphosphate 0.56% w/v to obtain ACC suspension comprising 10% of sodium triphosphate. The final composition comprised 73.53 mM of $CaCO_3$ in the water suspension.

SBC and CCC were dissolved or dispersed in water such that the concentration of carbonate was equal to that of ACC suspension (73.5 mM $CaCO_3$).

Figure 5:
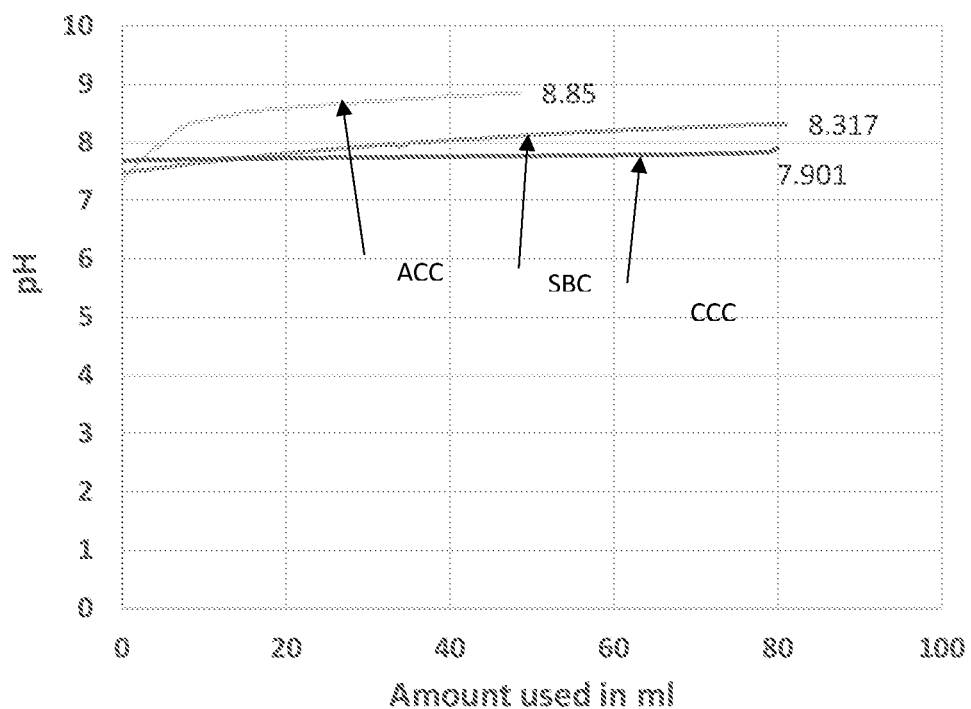
FIG. 5 shows a summary of titration procedures of DMEM/F12 with different types of carbonate sources.
Figure 6:
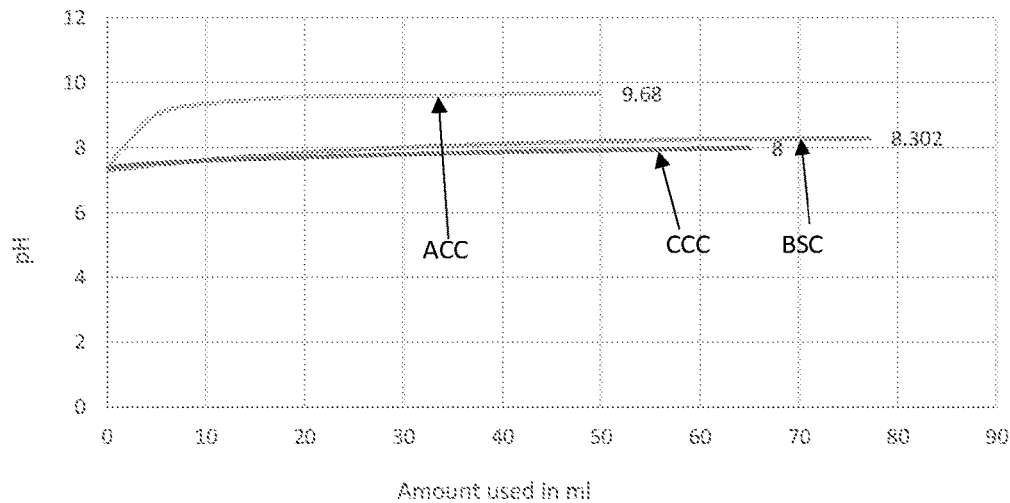
FIG. 6 shows a summary of the titration procedures of DPBS with different types of carbonate sources.

The dispersions or SBC solution of the different carbonate sources were slowly and continuously added to the 2 different media. The addition was done until a pH plateau was accomplished or the level of the solution reached the end of the capacity of the used container (~130 ml). The results are shown in FIGS. 5 and 6 and in Table 2.

TABLE 2

Influence of carbonate source of pH of two buffers

| Sort of Carbonate and the titrated solution | Amount in ml that was needed to reach pH 8 | Final pH |
| --- | --- | --- |
| ACC added to DPBS | 2.4 | 8.27 |
| SBC added to DPBS | 76.4 | 8.30 |
| CCC added to DPBS | 65 | 8 |
| ACC added to DMEM/F12 + 10% FBS | 7.5 | 8.27 |
| SBC added to DMEM/F12 + 10% FBS | 77 | 8.3 |
| CCC added to DMEM/F12 + 10% FBS | 80 | 7.90 |

As demonstrated in this example, the amount of ACC, needed to reach pH 8, was remarkably lower than the amount of both SBC solution and the CCC suspension. This is in-spite of the lower solubility of ACC relative to SBC. SBC, which is the substance tried previously for improving athlete performance, is not significantly different than the highly insoluble CCC in its capability (very slow) to reach higher pH levels.

Example 5. Comparative Effect of the Capability of Nanometric ACC Versus Nanometric CCC to Restore pH after Acidification of a Buffer System In this experiment the ability of ACC formulated with different stabilizers to affect the pH of medium supplemented with 10% (v/v) serum was evaluated in comparison to 2 different sources of CCC.

The experiment's solution was prepared by mixing 18 ml of a commercial medium (DMEM/F12, Biological Industries, Beit Haemek, Israel) and 2 ml of fetal bovine serum (FBS, Biological Industries, Beit Haemek, Israel). The solution was placed inside a sterile tissue sample cup and a hole was punched out at its top into which a pH probe was inserted. The cup was placed over a magnetic stirrer (JB-10 stirrer, Inesa, China) and during the procedure the solution was constantly stirred. A pH meter (MesuLab, PXSJ-216F ion meter, MRC, Israel) was connected to a PC for continuous measurement of the pH values using REXDC2.0 software.

An amount of 20.5 µl of lactic acid was added to the solution in order to reduce the pH to a slightly acidic pH in the range of 6.8. After a few seconds, 3 ml of various nanometric ACC or CCC suspensions having concentrations of 0.06%, freshly prepared (either in-situ or by suspending pre-made powders) were added to the acidified solution in each of the experiments. The procedure was repeated several times with:
1. ACC stabilized by triphosphate (TP), generated in-situ by mixing 4 solutions (calcium chloride, sodium carbonate and 2 solutions of TP, in an appropriate order.
2. ACC stabilized by triphosphate (TP), generated in-situ by mixing 2 solutions, in an appropriate order.
3. ACC stabilized by triphosphate (TP), generated and dried before its resuspension in water at equivalent weight of the above suspensions.
4. Nanometric crystalline calcium carbonate (CCC) that was prepared similarly to the above ACC but without the stabilizer. The powder was resuspended at the same concentrations as above.
5. Commercial nanometric CCC, suspended at the same concentration of the above solutions.

Figure 7:
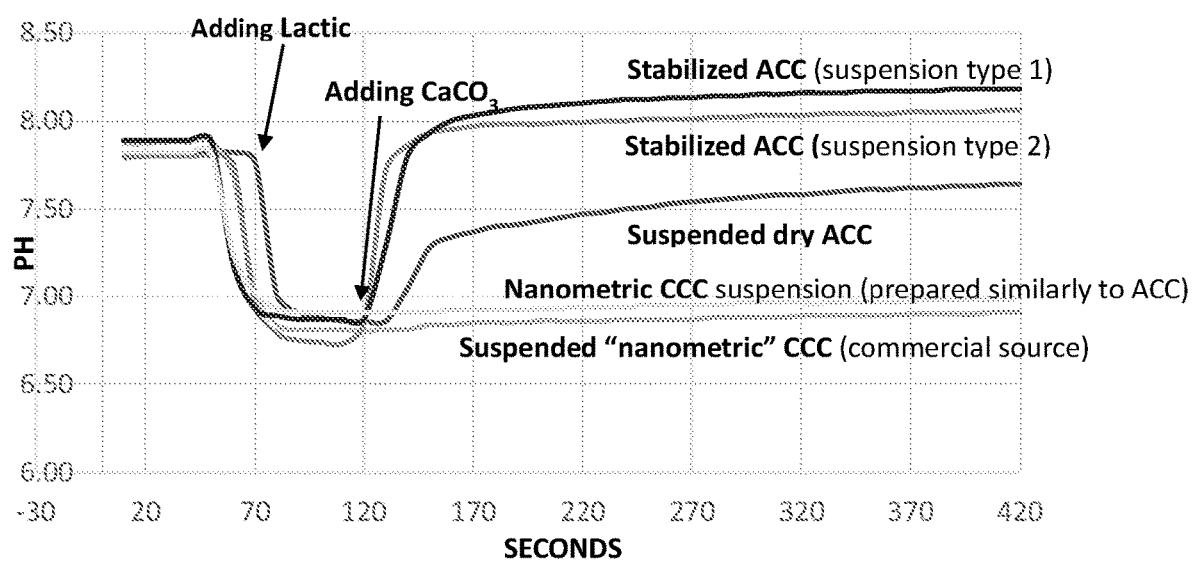
FIG. 7 shows the effect of various $CaCO_3$ sources on pH of a medium supplemented with lactic acid to decrease the pH to ~pH 6.8.

The results are presented in FIG. 7, which demonstrates the effect of the various ACC and CCC suspensions, added to the medium containing 10% serum. Initially, the pH was reduced by adding lactic acid to around 6.8. After adding all 3 types of ACC suspensions, there was an immediate and significant increase of the pH due to partial ACC dissolution to the levels of 7.9, 7.8 and 7.3, respectively to Experiments 1, 2, and 3 (i.e., immediate reduction of the $H^+$ concentration by a factor between 5 to 10. Then, the increase of the pH continues at a much slower rate and stops after about 500 seconds at pHs of 8.2, 8.1, and 7.6, respectively. It should be noted that the ACC in Experiment 4 is less reactive than the in-situ suspensions, due to excessive agglomerations, but it still provides one order of magnitude better reactivity with the acidic ions.

The two experiments with the CCC nanoparticles indicates almost no change in the pH. Hence, lower pH levels are required to activate and accelerate their dissolutions.

Although the present invention has been described herein above by way of preferred embodiments thereof, it can be modified, without departing from the spirit and nature of the subject invention as defined in the appended claims.

The invention claimed is:

1. A method for improving an athletic performance of a subject, the method comprising:
administering to said subject a composition comprising amorphous calcium carbonate (ACC) stabilized by at least one stabilizer.
2. The method according to claim 1, wherein improving the athletic performance comprises improving in at least one of strength, endurance, athletic achievements, or shortening the time for recovery.
3. The method according to claim 2, wherein improving the athletic performance comprises improvement of aerobic activity, anaerobic activity, or both.
4. The method according to claim 1, wherein improving the athletic performance comprises improving muscle performance.
5. The method according to claim 4, wherein improving muscle performance comprises at least one improvement selected from the group consisting of improving muscle strength, improving muscle endurance, increase muscle power, reducing muscle fatigue, improving physical mobility, shortening the time for recovery of muscles from intense physical activity, and any combination thereof.
6. The method according to claim 4, wherein the muscle is a healthy muscle.

7. The method according to claim 4, wherein the muscle includes at least one member selected from the group consisting of skeletal, cardiac, and smooth muscle.

8. The method according to claim 5, wherein improvement in physical mobility comprises an improvement in joint mobility and flexibility.

9. The method according to claim 5, wherein the intense physical activity is a short or a long term activity.

10. The method according to claim 1, wherein the subject is an athlete.

11. The method according to claim 1, administering to said subject a composition comprising ACC stabilized by at least one stabilizer comprises administering from about 5 to about 200 mg/kg/day of the stabilized ACC.

12. The method according to claim 1, wherein the administering comprises administration of 1, 2, 3, 4, 5, 6, 7, 8, 9, 10, 11 or 12 separate doses per day.

13. The method according to claim 1, wherein administering is selected from at least one of sublingual, oral, or by a combination of oral and sublingual administering of the composition.

14. The method according to claim 13, wherein the composition for sublingual administration is a powder composition comprising secondary particles of ACC having a size of below 500 μm.

15. The method according to claim 1, wherein the at least one stabilizer includes at least one member selected from the group consisting of polyphosphates, organic acids, phosphorylated amino acids, phosphorylated, phosphonated, sulfated or sulfonated organic compounds, phosphoric or sulfuric esters of hydroxy carboxylic acids, bisphosphonates, organic polyphosphates, polyphosphates, hydroxyl bearing organic compounds, derivatives thereof, proteins, and any combinations thereof.

16. The method according to claim 15, wherein the at least one stabilizer is selected from the group consisting of triphosphate or a salt thereof, phosphoserine, citric acid, sodium triphosphate and citric acid, adenosine triphosphate, adenosine diphosphate, phytic acid, etidronic acid, pyrophosphate, polyphosphate, hexamethaphosphate, ethanol, and any combination thereof.

17. The method according to claim 1, wherein the composition is formulated as a food supplement.

18. The method according to claim 1, wherein the active agent of the composition consists essentially of an amorphous calcium carbonate (ACC) stabilized by at least one stabilizer.

19. The method according to claim 1, wherein the composition consists essentially of an amorphous calcium carbonate (ACC) stabilized by at least one stabilizer.

* * * * *